(12) United States Patent
Wiater

(10) Patent No.: US 11,678,921 B2
(45) Date of Patent: Jun. 20, 2023

(54) METHODS OF LONG BONE REPAIR UTILIZING CONTINUOUS COMPRESSION IMPLANTS

(71) Applicant: DePuy Synthes Products, Inc., Raynham, MA (US)

(72) Inventor: Patrick Wiater, Bingham Farms, MI (US)

(73) Assignee: DePuy Synthes Products, Inc., Raynham, MA (US)

(*) Notice: Subject to any disclaimer, the term of this patent is extended or adjusted under 35 U.S.C. 154(b) by 252 days.

(21) Appl. No.: 17/119,276

(22) Filed: Dec. 11, 2020

(65) Prior Publication Data
US 2021/0177470 A1     Jun. 17, 2021

Related U.S. Application Data

(60) Provisional application No. 62/947,638, filed on Dec. 13, 2019.

(51) Int. Cl.
*A61B 17/88*     (2006.01)
*A61B 17/064*    (2006.01)
(Continued)

(52) U.S. Cl.
CPC .......... *A61B 17/88* (2013.01); *A61B 17/0642* (2013.01); *A61B 17/7225* (2013.01); *A61B 17/8004* (2013.01); *A61B 2017/681* (2013.01)

(58) Field of Classification Search
CPC .......... A61B 17/0642; A61B 2017/681; A61B 17/72; A61B 17/7225; A61B 17/80; A61B 17/8004; A61B 17/8019; A61B 17/8061; A61B 17/809; A61B 17/8866; A61B 17/88
See application file for complete search history.

(56) References Cited

U.S. PATENT DOCUMENTS 4,263,904 A * 4/1981 Judet .................. A61B 17/68
                                                    606/281
5,053,038 A * 10/1991 Sheehan ............ A61B 17/0642
                                                    606/75

(Continued)

OTHER PUBLICATIONS

Meinberg et al., Fracture and Dislocation Classification Compendium, Journal of Orthopaedic Trauma, Jan. 2018, vol. 32, No. 1 Supplement.

*Primary Examiner* — Larry E Waggle, Jr.
(74) *Attorney, Agent, or Firm* — BakerHostetler

(57) ABSTRACT

The present disclosure is directed to a method of surgical repair utilizing a continuous compression staple for an orthopedic injury site having a long bone fracture defining a fracture boundary between a first bone fragment and a second bone fragment. The method can include the steps of aligning the fragments, applying a temporary compressive force to the aligned fragments, inserting a compression staple in a tensioned state into the first and second bone fragments such that it traverses the fracture boundary, releasing tension in the compression staple such that the staple exerts a continuous compressive force to the first and second bone fragments, and securing a neutralization implant to the long bone. The disclosure further includes kits and systems for performing the disclosed surgical methods.

25 Claims, 19 Drawing Sheets

(51) Int. Cl.
    *A61B 17/80*     (2006.01)
    *A61B 17/72*     (2006.01)
    *A61B 17/68*     (2006.01)

(56) References Cited

U.S. PATENT DOCUMENTS

| | | | |
|---|---|---|---|
| 10,117,647 B2 * | 11/2018 | Cheney | A61B 17/064 |
| 2016/0324555 A1 * | 11/2016 | Brumfield | A61B 17/8014 |
| 2017/0056081 A1 * | 3/2017 | Langdale | A61B 17/8057 |

* cited by examiner

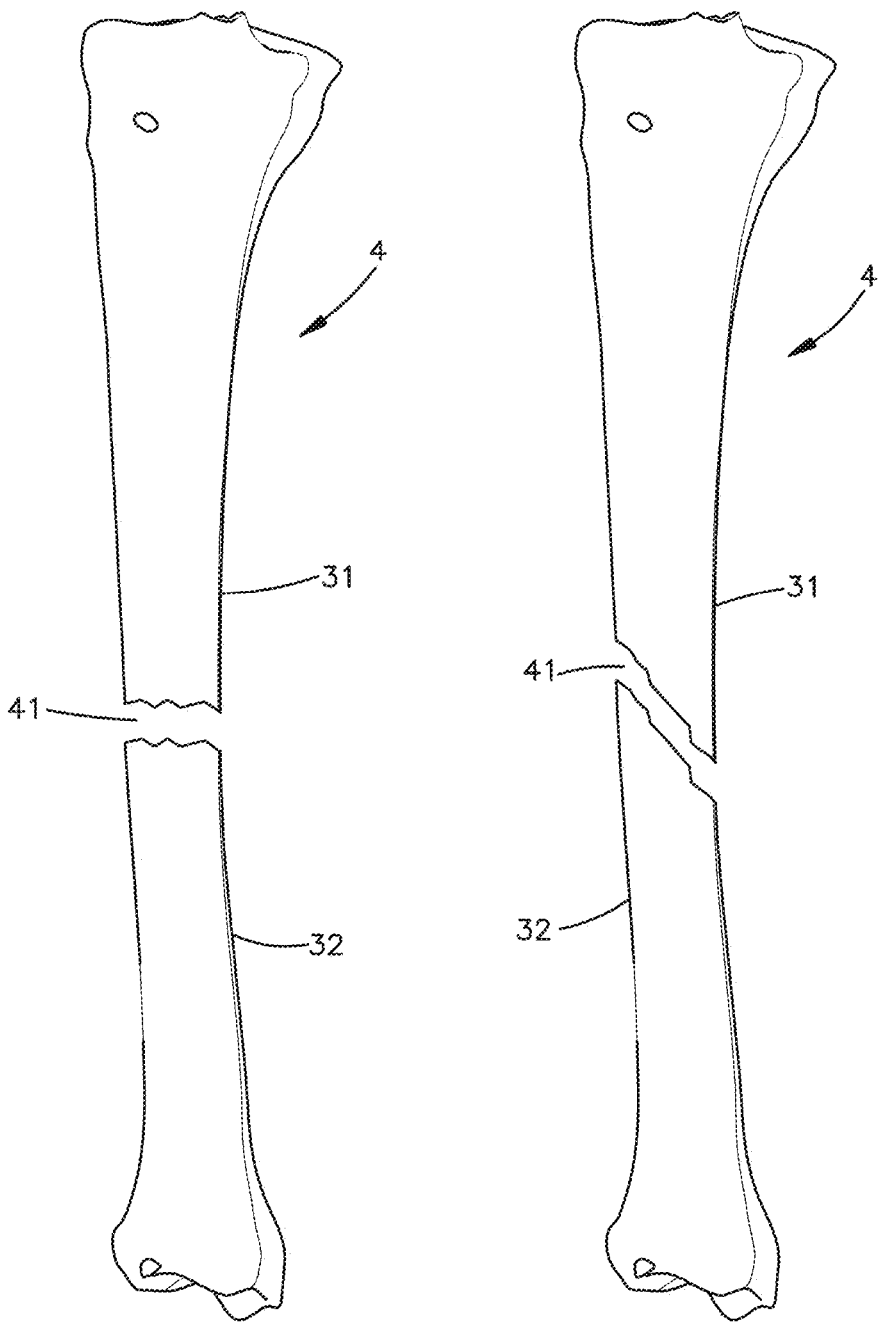

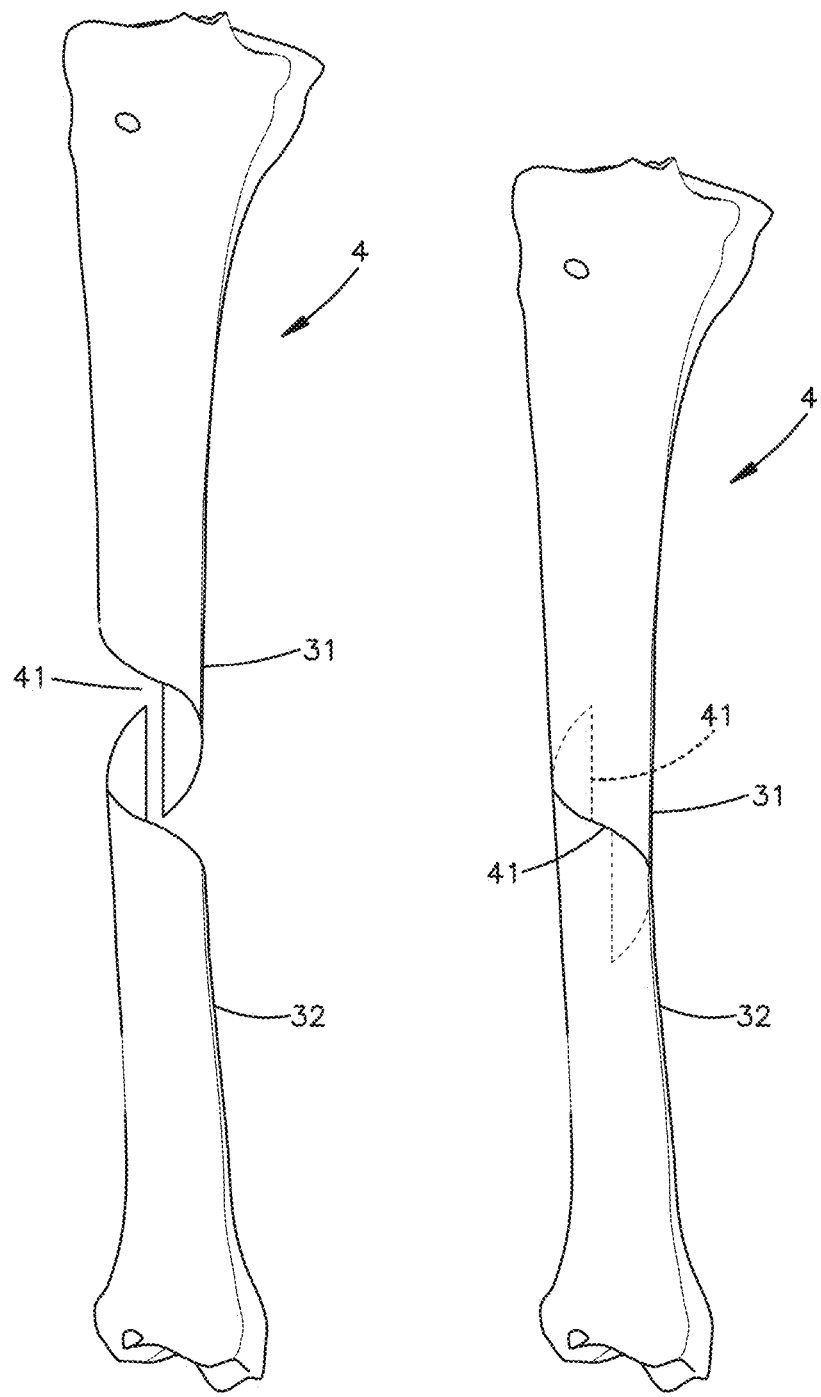

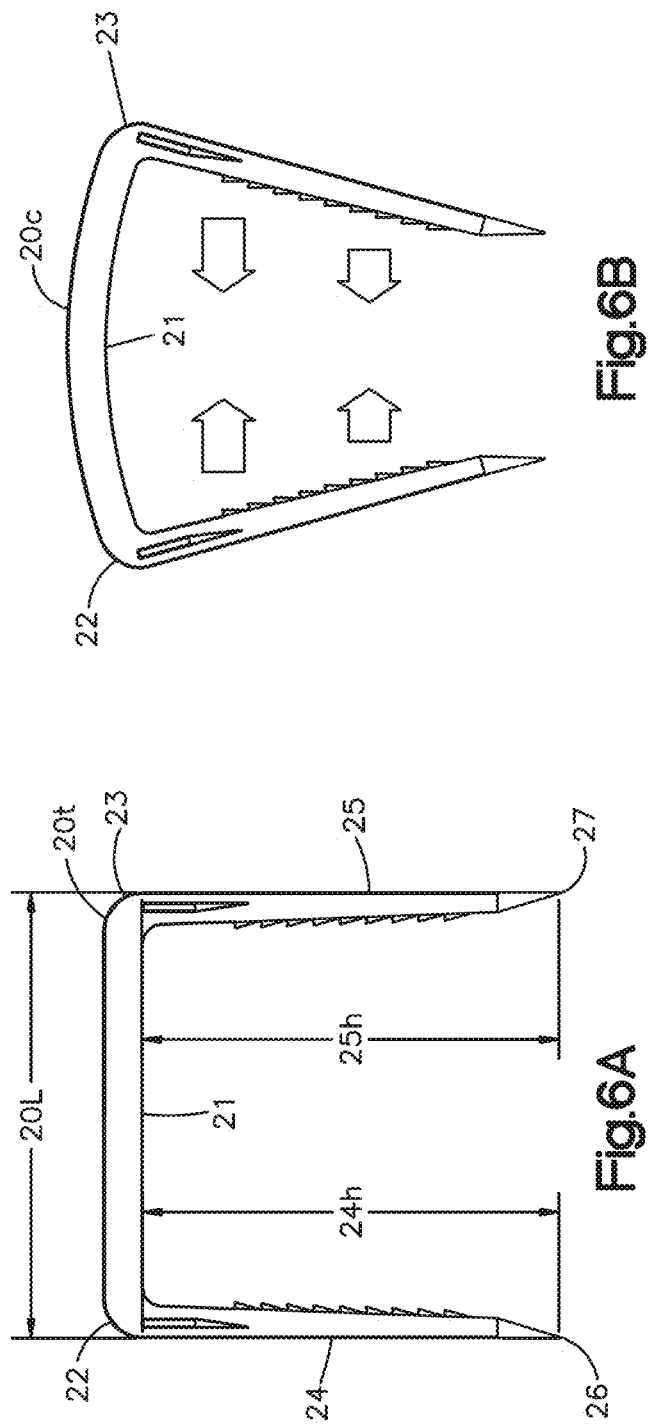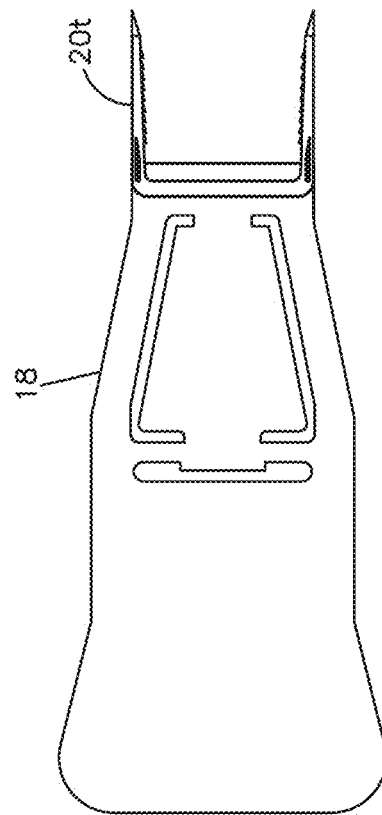

METHODS OF LONG BONE REPAIR UTILIZING CONTINUOUS COMPRESSION IMPLANTS

CROSS REFERENCE TO RELATED APPLICATIONS

This application claims the benefit of U.S. Provisional Application No. 62/947,638, filed on Dec. 13, 2019, the contents of which are hereby incorporated by reference in their entirety.

FIELD OF THE DISCLOSURE

The present disclosure is directed to methods of surgical repair of a fracture in a long bone utilizing a surgical construct including at least one compression stable and a neutralization implant.

BACKGROUND

Current methods for repair of fractures in long bones rely upon the use of lag screws, compression plates, or articulated tensioning devices to provide the necessary alignment and compression of the adjoining bone fragments. Lag screws (also referred to as "interfragmentary compression screws") can fail to gain purchase, and therefore proper compression, where there is a lack of sufficient cortical bone, such as in the diaphyseal region where the bone shaft is narrowest, or where there is poor cortical bone density, such as in the case of osteoporotic bone. Compression plates often require precise contouring to be effective and can additionally suffer from poor purchase of the bone screws securing the plate. Articulated tensioning devices are complex tool systems that are difficult to use correctly and require substantial amount of time to set the bone fragments as well as surgical space to be utilized effectively. Moreover, all three methods suffer from the same problem in that they only provide static compression to the fracture repair area. Once the screws are secured into the bone, the compression force does not become any greater; and, in certain cases, over time the compression force can drop to a level where malunion or non-union of the bone fragments occurs.

FIGS. 1A-B illustrate a problem associated with current long bone fracture repair techniques. FIGS. 1A-B are x-rays of an oblique diaphyseal fracture of the ulna of a 69-year-old woman. This fracture was initially repaired using a lag screw and a neutralization plate (also known as a stabilization plate or a bridge plate). The x-rays shown here were taken 6 weeks after surgical repair. As can be seen, the lag screw did not secure the adjacent bone fragments and failed to provide proper compression at the fracture site, which caused non-union of the bone fragments, and additionally caused the neutralization plate to break. Whether due to poor bone density at the fracture site, or an insufficient amount of cortical bone for the screw to gain purchase, the fact remains that the lag screw compression technique did not provide complete osteosynthesis to the ulna. Ultimately, this type of failed static compression technique requires an additional surgery to repair.

SUMMARY

The present inventor has identified a need in the surgical arts for improving the repair of fractured long bones that reduces the problems associated with static compression fixation in long bones as well as reducing dependence on the quality and quantity of cortical bone at the long bone repair site. The present inventor has surprisingly found that the use of continuous compression staples as a replacement to existing static compression methods provides unexpected and superior results.

Accordingly, the present disclosure is directed to methods of surgical repair of a long bone utilizing a surgical construct including at least one compression staple and a neutralization implant; the method including the steps of:

identifying an orthopedic injury site having a fracture of a long bone, the fracture defining a fracture boundary between a first bone fragment and a second bone fragment of the long bone;

aligning the first bone fragment and the second bone fragment to contact one another along at least a portion of the fracture boundary in anatomically correct position;

applying a temporary compressive force to the first and second bone fragments;

during the application of the temporary compressive force, inserting at least one compression staple into the first and second bone fragments such that the at least one compression staple traverses the fracture boundary, where the at least one compression staple is inserted in a first tensioned state;

releasing tension in the at least one compression staple such that the staple transitions from the first tensioned state to a second compressed state that exerts a continuous compressive force to the first and second bone fragments;

securing a neutralization implant to the long bone, the neutralization implant defining one or more apertures configured to receive a bone fastener, by applying the bone fastener through the one or more apertures and the long bone; and, removing the temporary compressive force.

According to another embodiment, the step of inserting the at least one compression staple includes inserting the at least one compression staple such the compression staple traverses the fracture boundary in a direction substantially normal to the fracture boundary. According to a further embodiment, the step of inserting the at least one compression staple includes inserting the at least one compression staple such that the at least one compression staple traverses the fracture boundary in a direction substantially parallel to the temporary compressive force.

According to one embodiment, the step of applying temporary compressive force creates a shear force at the fracture boundary configured to force translation of the first and second bone fragments relative to each other in the direction of the shear force, where the continuous compressive force of the at least one compression staple applies a net compression force across the fracture boundary that is substantially normal to the direction of shear force, and where the net compressive force is greater than the shear force.

According to yet another embodiment, the step of applying temporary compressive force creates a shear force at the fracture boundary configured to force translation of the first and second bone fragments relative to each other in the direction of the shear force, and the methods can further include:

prior to inserting the at least one compression staple, applying a buttress plate to the first and second bone fragments such that the buttress plate traverses the fracture boundary, and securing the buttress plate to only one of the first or second bone fragments such that the other of the first or second bone fragments is not secured to the buttress plate;

where the buttress plate is configured to inhibit the translation of the first and second bone fragments in the direction of the shear force.

According to still other embodiments, the at least one compression staple includes a first compression staple and a second compression staple and the step of inserting at least one compression staple and the step of releasing tension in the at the least one compression staple includes:

inserting the first compression staple into the first and second bone fragments such that the first compression staple traverses the fracture boundary, where the first compression staple is inserted in a first tensioned state;

releasing tension in the first compression staple such that the first compression staple transitions from the first tensioned state to a second compressed state that exerts a continuous compressive force to the first and second bone fragments;

inserting the second compression staple into the first and second bone fragments such that the second compression staple traverses the fracture boundary, where the second compression staple is inserted in a first tensioned state; and releasing tension in the second compression staple such that the second compression staple transitions from the first tensioned state to a second compressed state that exerts a continuous compressive force to the first and second bone fragments.

According to further embodiments utilizing the first and second compression staples, the step of inserting the second compression staple includes inserting the second compression staple such that the second compression staple traverses the fracture boundary in a direction substantially normal to the fracture boundary. In additional embodiments, the second compression staple is inserted in a direction substantially parallel to the temporary compressive force.

According to additional embodiments, the continuous compressive force of the first and second compression staples exerts a combined net compression force applied across the fracture boundary that is substantially normal to the direction of shear force. According to further embodiments, the net compressive force is greater than the shear force.

According to certain embodiments of the present disclosure, the long bone fracture includes at least a first fracture boundary and second fracture boundary such that the fracture boundary between the first bone fragment and the second bone fragment is the first fracture boundary and the fracture boundary between a third bone fragment and either the first bone fragment or the second bone fragment, or both, is the second fracture boundary. In embodiments including at least a first and second fracture boundary, the at least one compression staple includes at least a first compression staple and a second compression staple, where the first compressions staple is the at least one compression staple that is inserted at the fracture boundary between the first and second bone fragments. The methods can therefore further include:

aligning the third bone fragment to contact either of the first bone fragment or the second bone fragment, or both, along at least a portion of the second fracture boundary in anatomically correct position;

applying a temporary compressive force to the third bone fragment and either of the first bone fragment or the second bone fragment, or both;

during the application of the temporary compressive force to the third bone fragment, inserting the second compression staple into the third bone fragment such that the second compression staple traverses the second fracture boundary, wherein the second compression staple is inserted in a first tensioned state; and, releasing tension in the second compression staple such that the second compression staple transitions from the first tensioned state to a second compressed state that exerts a continuous compressive force to the third bone fragment and either of the first bone fragment or the second bone fragment, or both.

According to certain additional embodiments, the method can further include inserting the second compression staple such the second compression staple traverses the second fracture boundary in a direction substantially normal to the second fracture boundary; or additionally, inserting the second compression staple such the second compression staple traverses the second fracture boundary in a direction substantially parallel to the temporary compressive force to the third bone fragment. In embodiments where the temporary compressive force applied to the third bone fragment generates a shear force at the second fracture boundary, the method can further include inserting the second compression staple such that it traverses the second fracture boundary in a direction substantially normal to the direction of shear force.

According to further embodiments where the temporary compressive force applied to the third bone fragment generates a shear force at the second fracture boundary, the method can include:

prior to inserting the second compression staple, applying a buttress plate to the third bone fragment and either of the first bone fragment or the second bone fragment such that the buttress plate traverses the second fracture boundary, and securing the buttress plate to only one of the third bone fragment or the first or second bone fragments such that the other of the third bone fragment or the first or second bone fragments is not secured to the buttress plate;

where the buttress plate is configured to inhibit movement of the third bone fragment in a direction of the shear force.

According to additional embodiments of the present disclosure, a method of surgical repair of a long bone utilizing a surgical construct is described including at least one continuous compression staple and a buttress plate is described, the method including the steps of:

identifying an orthopedic injury site having a fracture of a long bone, the fracture defining a fracture boundary between a first bone fragment and a second bone fragment of the long bone;

aligning the first bone fragment and the second bone fragment to contact one another along at least a portion of the fracture boundary in anatomically correct position;

applying a temporary compressive force to the first and second bone fragments such that a shear force is created the fracture boundary configured to force translation of the first and second bone fragments relative to each other in the direction of the shear force;

during the application of the temporary compressive force, applying a buttress plate to the first and second bone fragments such that the buttress plate traverses the fracture boundary, and securing the buttress plate to only one of the first or second bone fragments such that the other of the first or second bone fragments is not secured to the buttress plate, wherein the buttress plate is configured to inhibit the translation of the first and second bone fragments in the direction of the shear force;

during the application of the temporary compressive force inserting at least one compression staple into the first and second bone fragments such that the at least one compression staple traverses the fracture boundary, wherein the at least one compression staple is inserted in a first tensioned state;

releasing tension in the at least one compression staple such that the staple transitions from the first tensioned state to a second compressed state that exerts a continuous compressive force to the first and second bone fragments; and, removing the temporary compressive force.

According to further embodiments of the present disclosure, a kit for use in the surgical repair of a long bone fracture is described including:

at least one compression staple configured to traverse a fracture boundary in a long bone between a first bone fragment and a second bone fragment; and, at least one neutralization implant.

In certain embodiments, the kit can additionally include at least one buttress plate.

According to still further embodiments of the present disclosure, a surgical construct system for use in the surgical repair of a long bone fracture is described including:

at least one compression staple configured to traverse a fracture boundary in a long bone between a first bone fragment and a second bone fragment;

at least one buttress plate configured to traverse the fracture boundary and, a neutralization implant.

BRIEF DESCRIPTION OF THE DRAWINGS

FIGS. 3A-E are front view schematic representations of exemplary fractures of a tibia;

FIGS. 4A-D are front view schematic representations of exemplary reduction and alignment of the tibia fractures shown in FIGS. 3B and 3C, respectively according to embodiments of the present disclosure;

FIGS. 6A-B are front views of a continuous compression staple according to embodiments of the present invention in a first tensioned state (FIG. 6A) and a second compressed state (FIG. 6B) (with arrows indicating direction of continuous compressive force);

FIG. 7 is a top view of a representative staple insertion tool with a continuous compression staple loaded in the tool in the first tensioned state according to embodiments of the present disclosure;

DETAILED DESCRIPTION

For the purpose of this application, terminology and definitions related to long bones and the types of fractures occurring in long bones is derived from the AO Classification that can be found in "Fracture and Dislocation Classification Compendium" J Orthop Trauma Volume 32, Number 1 Supplement, January 2018, which is hereby incorporated by reference in its entirety.

As used herein, the term "long bone" is limited to the humerus, radius, ulna, femur, tibia, and fibula of mammals.

According to the present disclosure, methods of surgical repair are described including the steps of:

identifying an orthopedic injury site having a fracture of a long bone, the fracture defining a fracture boundary between a first bone fragment and a second bone fragment of the long bone;

aligning the first bone fragment and the second bone fragment to contact one another along at least a portion of the fracture boundary in anatomically correct position;

applying a temporary compressive force to the first and second bone fragments;

during the application of the temporary compressive force, inserting at least one compression staple into the first and second bone fragments such that the at least one compression staple traverses the fracture boundary, where the at least one compression staple is inserted in a first tensioned state;

releasing tension in the at least one compression staple such that the staple transitions from the first tensioned state to a second compressed state that exerts a continuous compressive force to the first and second bone fragments;

securing a neutralization implant to the long bone, the neutralization implant defining one or more apertures configured to receive a bone fastener, by applying the bone fastener through the one or more apertures and the long bone; and, removing the temporary compressive force.

Figure 1A:
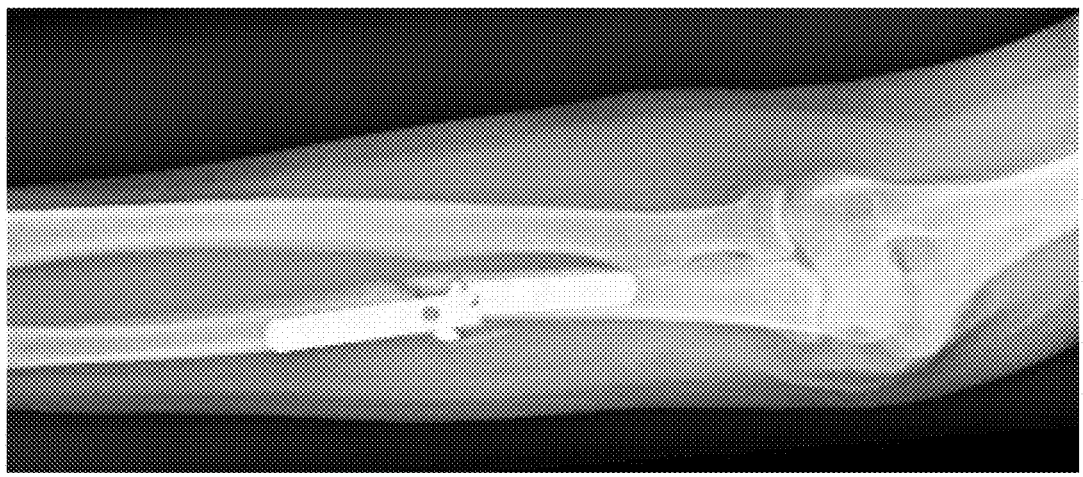
FIGS. 1A-B are x-rays of an ulna showing the failure of a lag screw compression surgery to align and compress adjoining bone fragments.
Figure 1B:
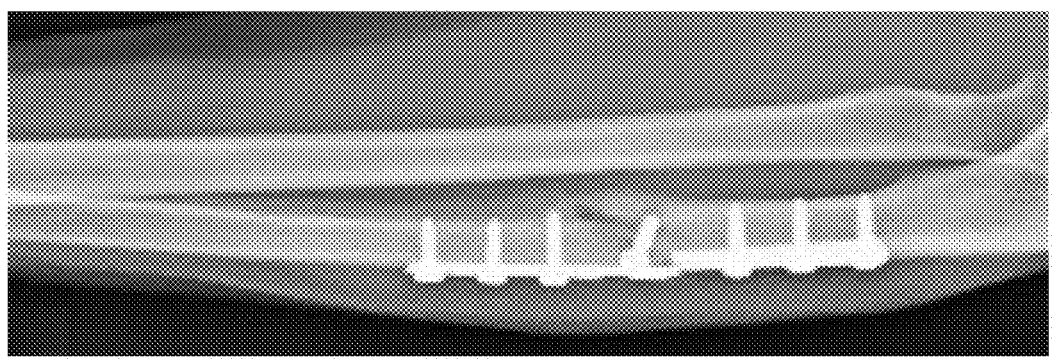
Figure 2:
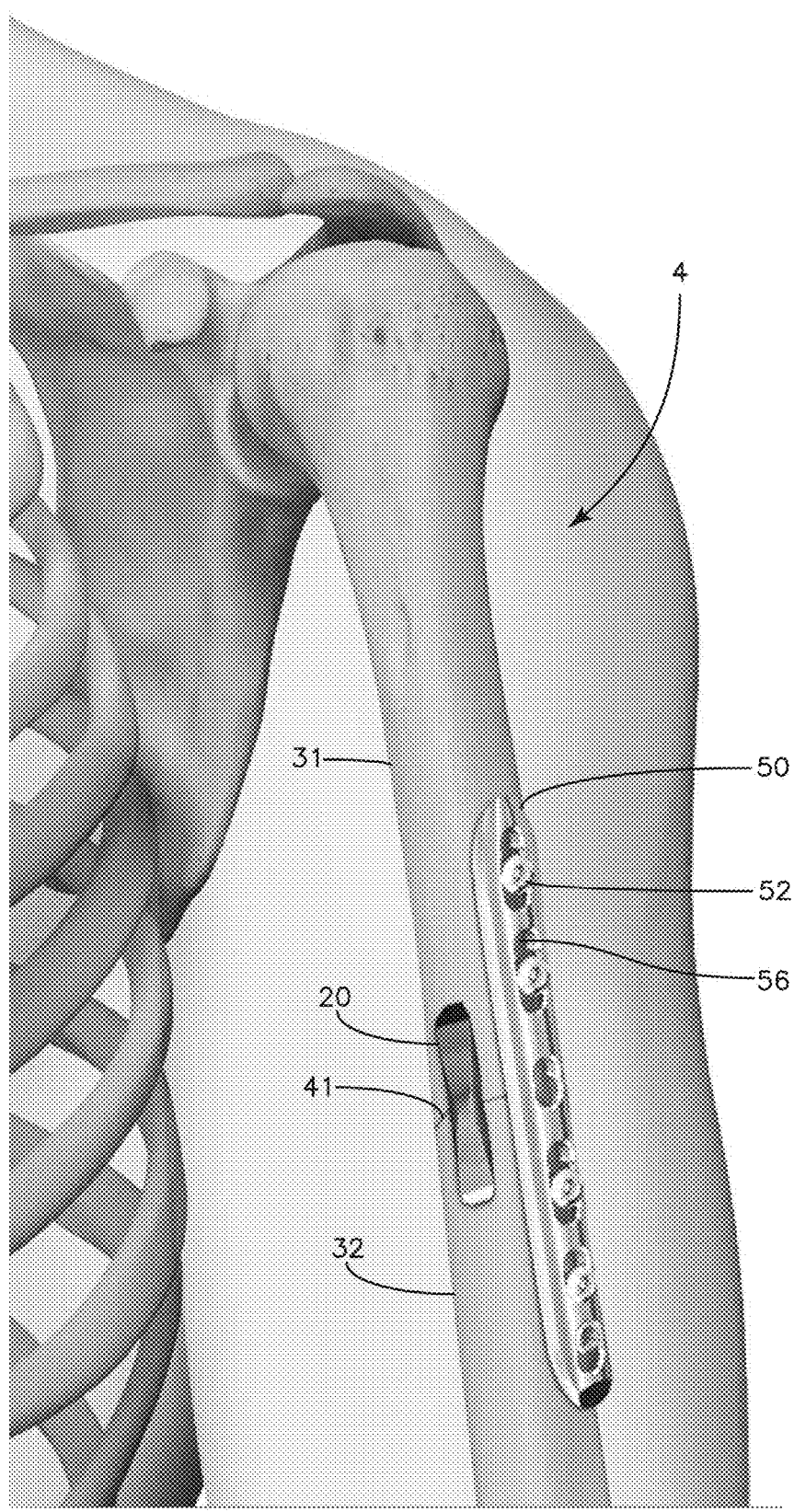
FIG. 2 is a front view schematic representation of a surgical repair of a transverse fracture of the diaphyseal region of the humerus according to methods of the present disclosure.

FIG. 2 shows a schematic representation of a completed surgical procedure according to exemplary methods of the present disclosure including repair of a long bone 4 utilizing a surgical construct including at least one continuous compression staple 20 and a neutralization implant 50. As shown, long bone 4 (here, the humerus) has a transverse fracture in the diaphyseal region of the humeral shaft, the fracture defining a fracture boundary 41 between a first bone fragment 31 and a second bone fragment 32. The compression staple 20 has been inserted into the first bone fragment 31 and the second bone fragment 32 and traverses the fracture boundary 41. The compression staple 20 applies a continuous compressive force to the first 31 and second 32 bone fragments to keep them in contact and anatomical alignment, which promotes proper bone healing of the humerus 4. Neutralization implant 50 has been secured to the long bone 4 to protect and maintain the integrity of the humerus during fracture healing. The neutralization implant 50 (as the name implies) neutralizes bending, rotational, and axial forces along long bone 4 to provide relative stability and to permit correct length, alignment, and rotation in the bone as the fracture heals. Exemplary classes of neutralization implants 50 can include intramedullary nails and bone plates configured for use with long bones, such as e.g., locking plates or bridge plates. In a preferred embodiment, the neutralization implant 50 does not facilitate or otherwise influence healing at the fracture site, and therefore preferably excludes implants such as lag screws and compression plates. In this exemplary embodiment, the neutralization implant 50 is a locking bone plate including one or more apertures 56 configured to receive a bone fastener 52 so as to secure the implant 50 to the long bone 4 and is fixed to each of the first 31 and second 32 bone fragments without compromising or otherwise interacting with fracture boundary 41.

According to the present disclosure, and with reference to FIGS. 3A-3E, methods of surgical repair are described that include the step of identifying an orthopedic injury site of a long bone 4 (as shown in FIGS. 3A-E, a tibia) that includes a fracture suitable for repair utilizing at least one continuous compression staple. While there are numerous types of long bone fractures and methods of characterizing fracture patterns, FIGS. 3A-E provide, for the purpose of example, categories of certain fractures that are suitable for surgical repair according to the present disclosure and are for the purpose of illustration only.

Figures 3C, 3D:
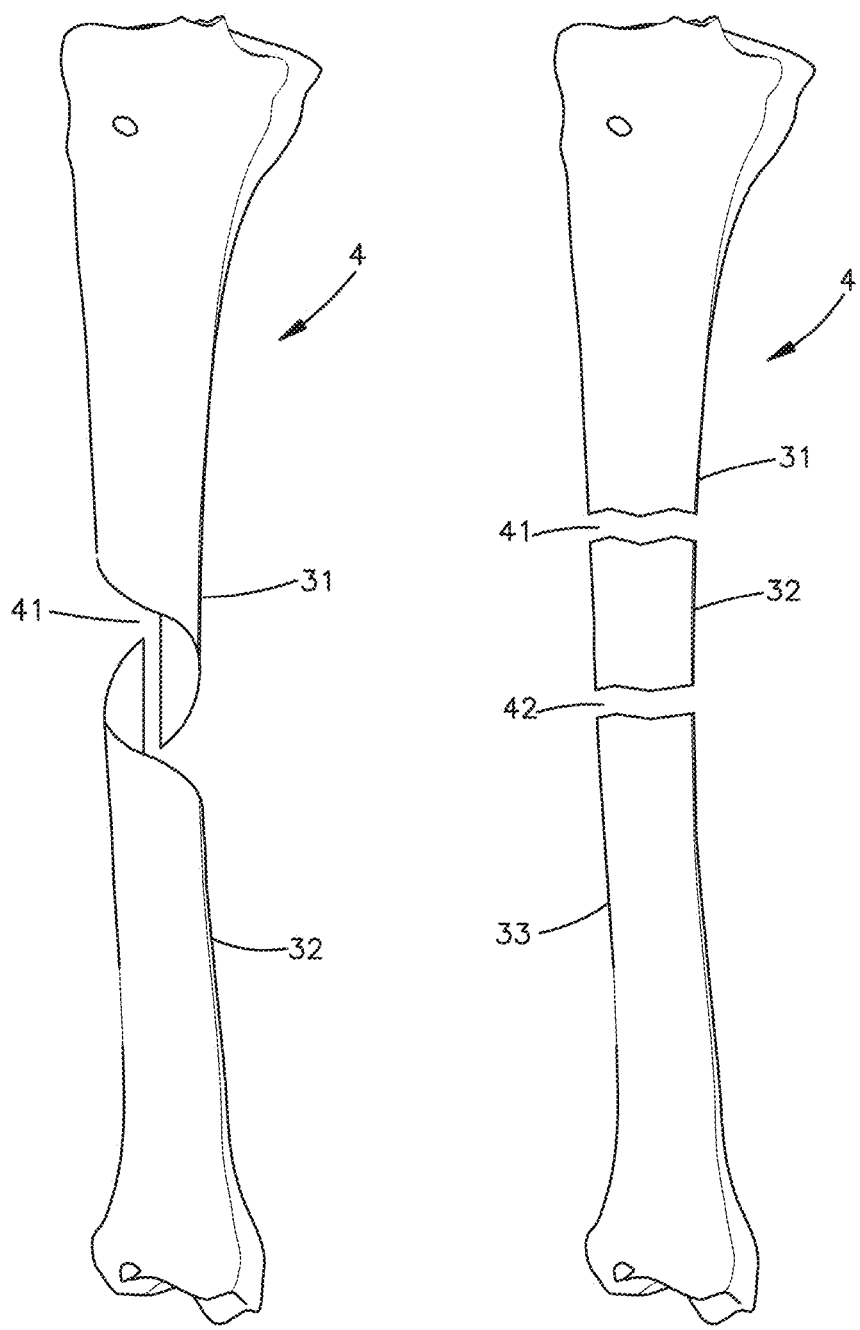

FIGS. 3A-C are representative of what are known in the AO classification as simple fractures consisting of a single fracture defining two bone segments of the long bone. FIG. 3A is a transverse fracture defining a fracture boundary 41 between first bone fragment 31 and second bone fragment 32. According to the AO classification, a transverse fracture is defined as a fracture having an angle relative to the short axis of the long bone 4 of between 0 and 30 degrees. FIG. 3B is an oblique fracture defining a fracture boundary 41 between first bone fragment 31 and second bone fragment 32. According to the AO classification, an oblique fracture is defined as a fracture having an angle relative to the short axis of the long bone 4 of greater than 30 degrees. FIG. 3C is a spiral fracture defining a fracture boundary 41 between first bone fragment 31 and second bone fragment 32. Spiral fractures typically have a fracture boundary 41 that spirals along the long axis of the bone and are accompanied by sharp or pointed edges.

Figure 3E:
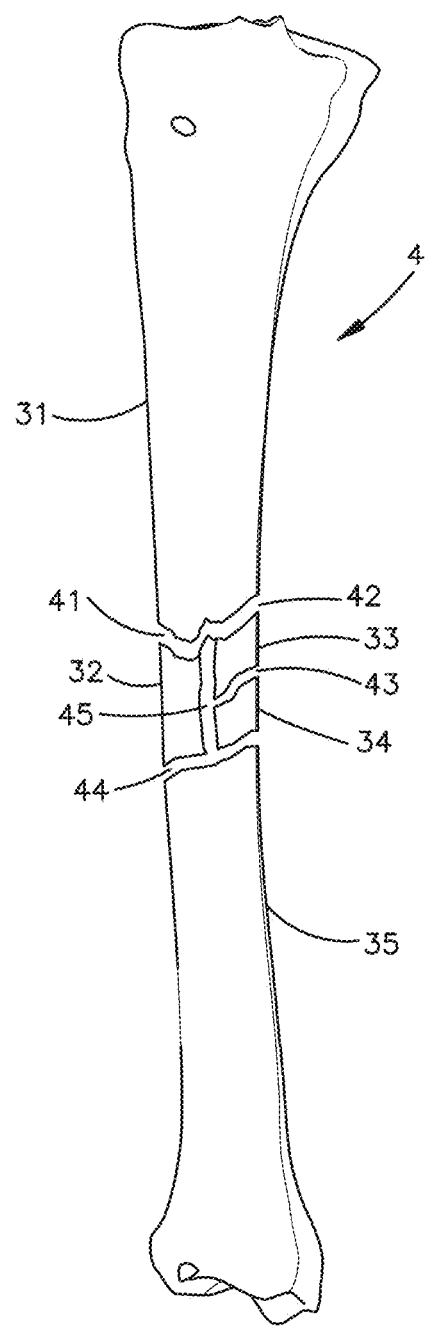

FIGS. 3D-E are representative of more complex long bone fractures. FIG. 3D-2E are representative of what are known in the AO classification as complex fractures where there is a lack of contact between the bone fragments including the ends (proximal, distal) of the long bone 4. FIG. 3D is a segmental fracture defining a first fracture boundary 41 between first bone fragment 31 and second bone fragment 32 and a second fracture boundary 42 between second bone fragment 32 and third bone fragment 33. As shown, the main proximal bone fragment 31 has no means of directly contacting the main distal bone fragment 33. Certain other segmental fractures (not shown) can be classified in the AO classification as wedge fractures (an intermediate fracture classification), where there is still a potential point of contact available between the main proximal and distal bone segments. Wedge fractures are considered suitable for surgical repair according to methods of the present disclosure. Returning to FIG. 3D, as shown, both first 41 and second 42 fracture boundary of the segmental fracture define substantially transverse fracture patterns; however, it should be appreciated that either or both fracture boundaries can assume different fracture patterns, such as e.g., oblique or spiral. FIG. 3E is known as a comminuted (i.e., multi-fragmentary) fracture. Comminuted fractures include a category of some of the most severe long bone fractures. They define a fracture including at least a first 31, second 32, and third 33 bone fragment, and where the fracture boundaries defining the bone fragments can intersect. Comminuted fracture boundaries can include fracture patterns that are transverse, oblique, or spiral. As shown in FIG. 3E, the fractured long bone 4 includes five bone fragments (31, 32, 33, 34, and 35) defining up to five fracture boundaries (41, 42, 43, 44, and 45).

Thus, according to embodiments of the present invention, the fracture of the long bone can include, traverse, oblique, spiral, segmental (including wedge), and comminuted, as well as combinations thereof. According to further embodiments, the fracture of the long bone can include certain regions of the long bone including the diaphyseal, metaphyseal, articular, and malleolar regions, as well as combinations thereof.

Figures 4A, 4B:
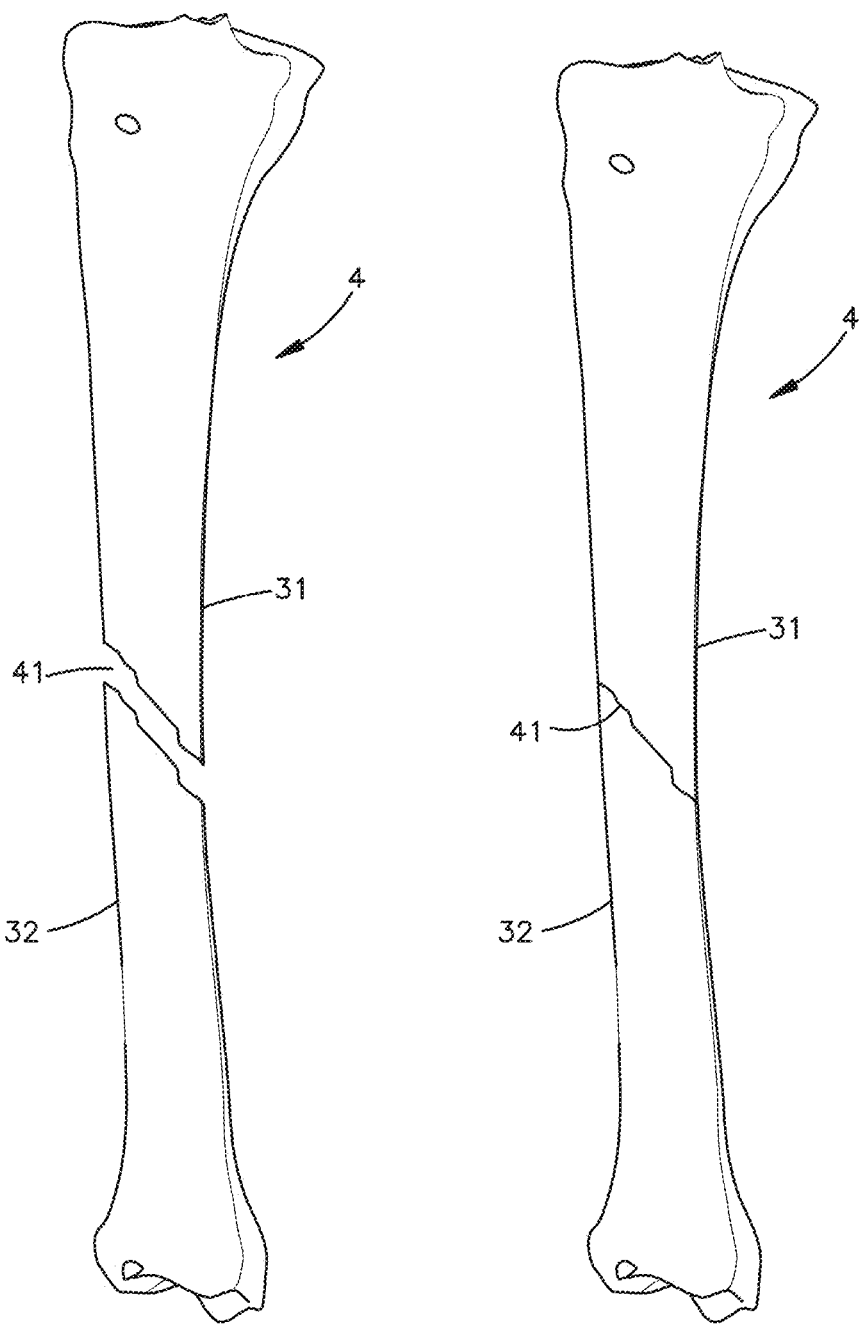

According to the present disclosure, methods of surgical repair are described that include the step of aligning the first bone fragment and the second bone fragment to contact one another along at least a portion of the fracture boundary in anatomically correct position. FIGS. 4A-D show exemplary alignments of first 31 and second 32 bone fragments at fracture boundary 41 of the long bone 4. FIGS. 4A-B show the reduction and anatomical alignment of a transverse fracture of the tibia in the diaphyseal region. FIGS. 4C-D show the reduction and anatomical alignment of a spiral fracture of the tibia in the diaphyseal region.

It should be appreciated that surgical techniques and procedures can vary among orthopedic surgeons in the case of complex fractures. With respect to multi-fragment long bone fractures, depending on a particular surgeon's preference for the sequence in which the reduction and repair of the collective bone fragments will occur, the numbering convention employed in the present disclosure with respect to bone fragments and fracture boundaries (i.e., a first bone fragment 31 or a first fracture boundary 41) is not meant to signify the order in which long bone 4 is actually repaired, but is merely for identification purposes. In other words, where multi-fragmentary fractures are described herein, it is equally within the scope of the disclosure that a second 32 and third 33 bone fragment are aligned or repaired before or after a first 31 and second 32, or a first 31 and third 33 bone fragment are aligned and repaired.

Figure 5:
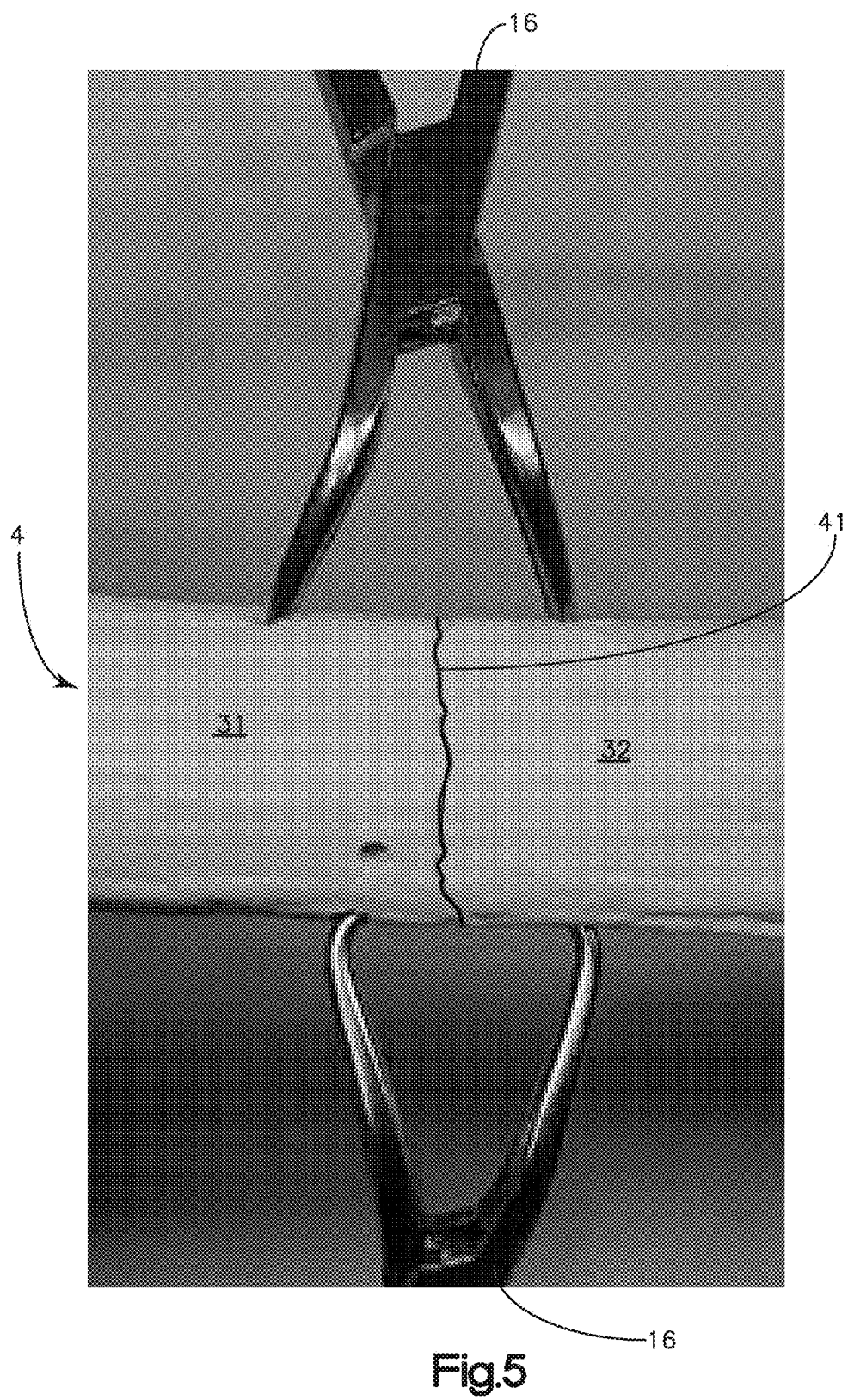
FIG. 5 is a top view photograph of a pair of bone reduction forceps applying temporary compressive force to bone fragments of a long bone according to embodiments of the present disclosure.

According to the present disclosure, and with reference to FIG. 5, methods of surgical repair are described that include the step of applying temporary compressive force to the first 31 and second 32 bone fragments. According to certain embodiments, the application of temporary compressive force can occur simultaneously with the previously described step of aligning. Alternatively, the step of applying temporary compressive force can occur after the step of aligning. As an example, one suitable tool 16 for applying temporary compressive force to the first 31 and second 32 bone fragments at the fracture boundary 41 is bone reduction forceps 16. As shown in FIG. 4, a pair of forceps 16 are applying temporary compression to first 31 and second 32 bone fragments across fracture boundary 41.

Figure 8:
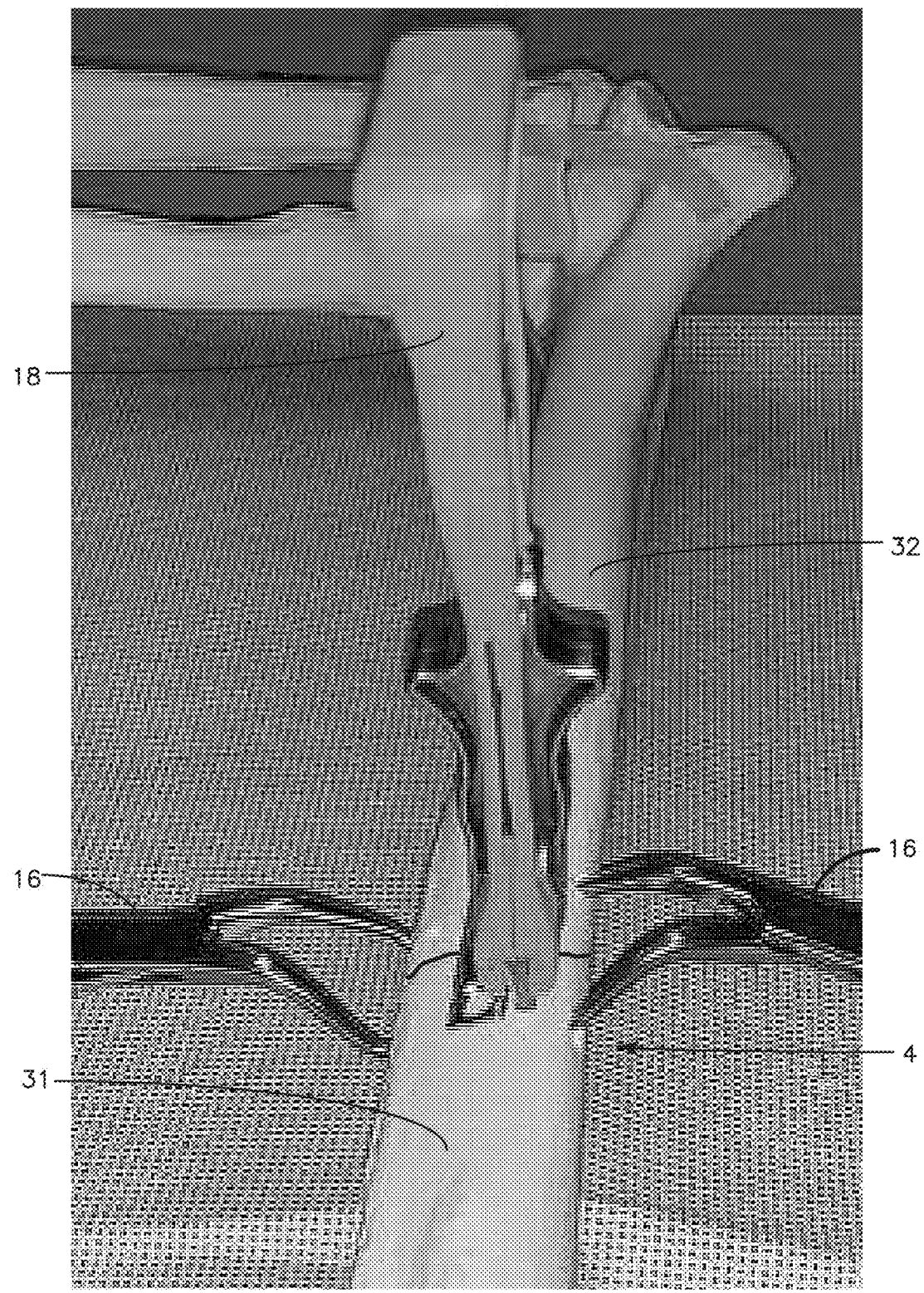
FIG. 8 is side perspective view photograph showing a long bone fracture with a pair of bone reduction forceps applying temporary compressive force to the bone fragments and a staple insertion tool inserting a continuous compression staple across a fracture boundary according to embodiments of the present disclosure.

According to the present disclosure, and with reference to FIGS. 6-8, methods of surgical repair are described that include, during the application of temporary compressive force, the step of inserting at least one compression staple 20 into the first 31 and second 32 bone fragments such that the at least one compression staple 20 traverses the fracture boundary 41.

According to certain embodiments, the at least one compression staple 20 defines a bridge 21 having a first end 22 and a second end 23, the bridge 20 defining a bridge length 20L extending between the first end 22 and a second end 23. Additionally, the at least one compression staple 20 defines a first leg 24 and a second leg 25, where the first leg 24 extends from the first end 22 of the bridge 21 to a first distal tip 26 and defines a first leg height 24*h*, and the second leg 25 extends from the second end 23 of the bridge 21 to a second distal tip 27 and defines a second leg height 25*h*. In certain embodiments, the bridge has a bridge length in the range of about 15 mm to about 25 mm. In further embodiments, the at least one compression staple 20 can further include a third leg 28 and fourth leg 29, wherein the third 28 and fourth 29 legs each extend from the bridge 21 between the first leg 24 and second leg 25 and in substantially the same direction as the first 24 and second 25 legs.

Preferably, the at least one compression staple 20 is inserted in a first tensioned state 20*t*. According to certain embodiments, compression staple 20 is made from a shape memory material such as a shape memory alloy. A preferred shape memory alloy is nitinol, which is an approximately 50%/50% titanium-nickel metal alloy. Due to the shape-memory properties, compression staple 20 can be mechanically or thermally deformed from its original configuration and return to its original state upon removal of the deformation force. According to the methods of surgical repair described herein, the deformation force can be a tensioning force. Referring to FIGS. 6A, compression staple 20 is shown in a tensioned state 20*t*, where the legs of the staple have been deformed by tension to approximate right angles with respect to the bridge of the staple. Referring to FIG. 6B, compression staple 20 is shown in a compressed state 20*c* where the legs of the staple have returned to their original configuration upon removal of the tensioning force and exert a continuous compressive force (arrows indicating relative movement and compression). Referring to FIG. 7, an exemplary staple insertion tool 18 is shown, with a compression staple 20 affixed in the tensioned state 20*t*. Referring to FIG. 8, insertion tool 18 is shown inserting a tensioned staple 20*t* (not shown) into first 31 and second 32 bone fragments across fracture 41 of long bone 4 during the application of temporary compressive force by a pair of bone reduction forceps 16. Once inserting of compression staple 20*t* is complete, it can be released from insertion tool 18, and upon release from insertion tool 18, tension in the compression staple 20 is likewise removed, causing compression staple 20*t* to transition from a tensioned state to a compressed state 20*c* that exerts a continuous compressive force to first 31 and second 32 bone fragments across fracture boundary 42.

Figure 9:
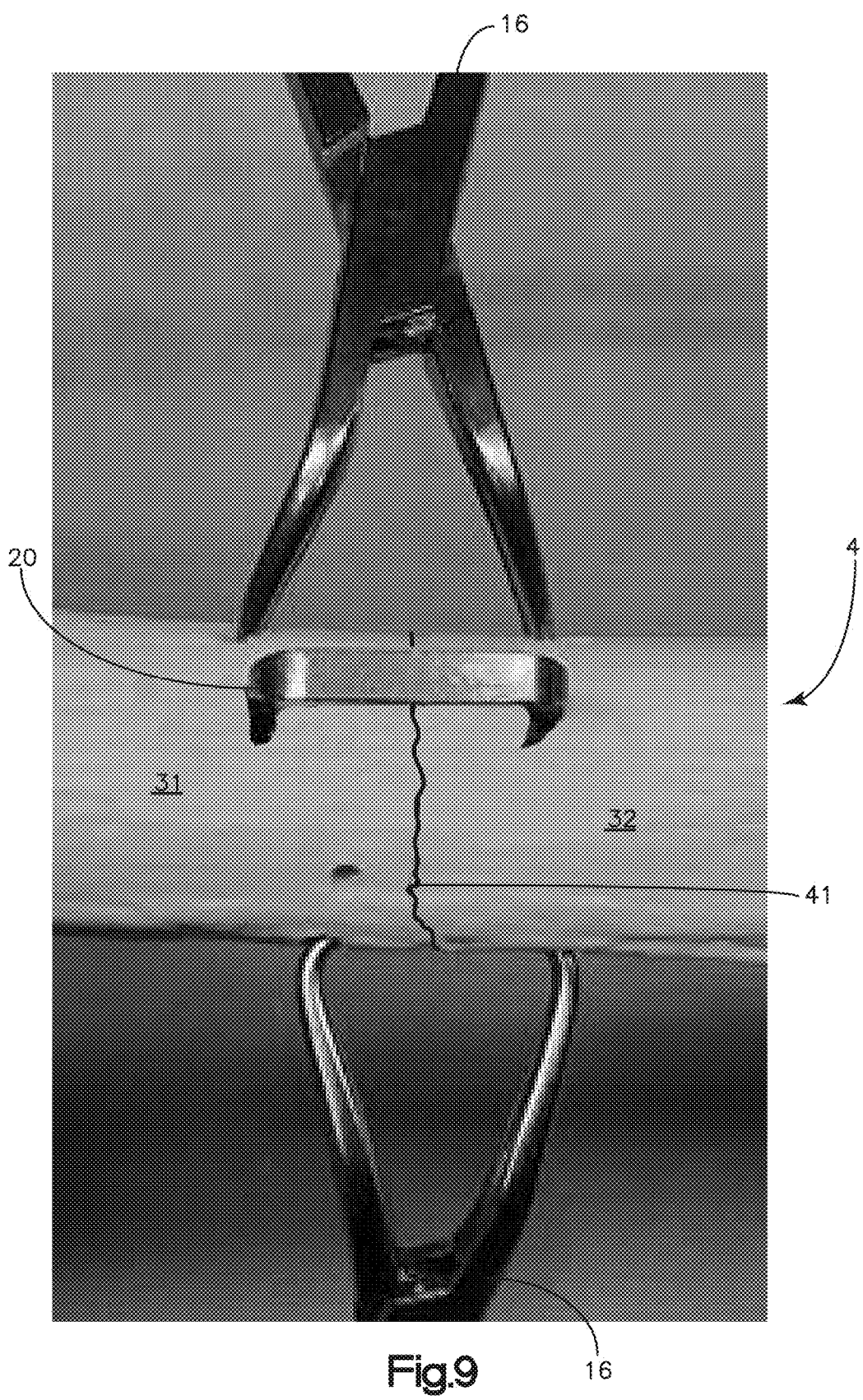
FIG. 9 is a top view photograph of a continuous compression staple inserted into a long bone and traversing a fracture boundary in a compressed state with a pair of bone reduction forceps applying a temporary compressive force according to embodiments of the present disclosure.

According to certain embodiments, and with reference to FIG. 9 the step of inserting the compression staple 20 is such that compression staple 20 traverses fracture boundary 41 in a direction substantially normal to fracture boundary 41. According to certain additional embodiments, the step of inserting the compression staple 20 is such that compression staple 20 traverses fracture boundary 41 in a direction substantially parallel to the temporary compressive force.

Figure 10A:
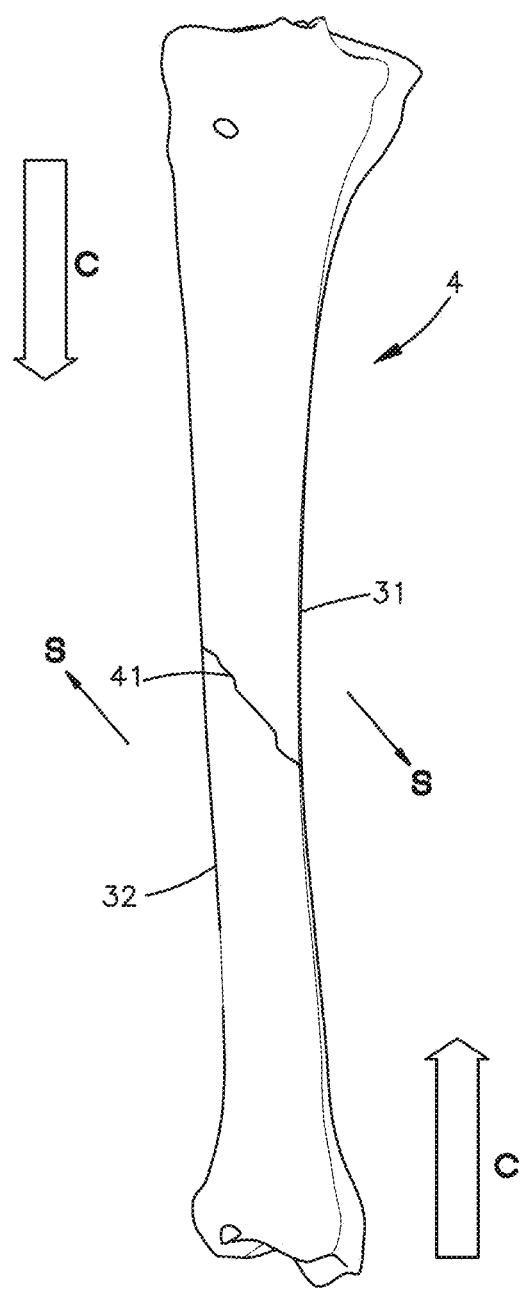
FIG. 10A is a schematic front view of an oblique fracture with a fracture boundary in the diaphyseal region of a tibia with arrows "C" indicating the application and direction of temporary compressive force and arrows "S" showing the generation and direction of a resultant shear force.
Figure 10B:
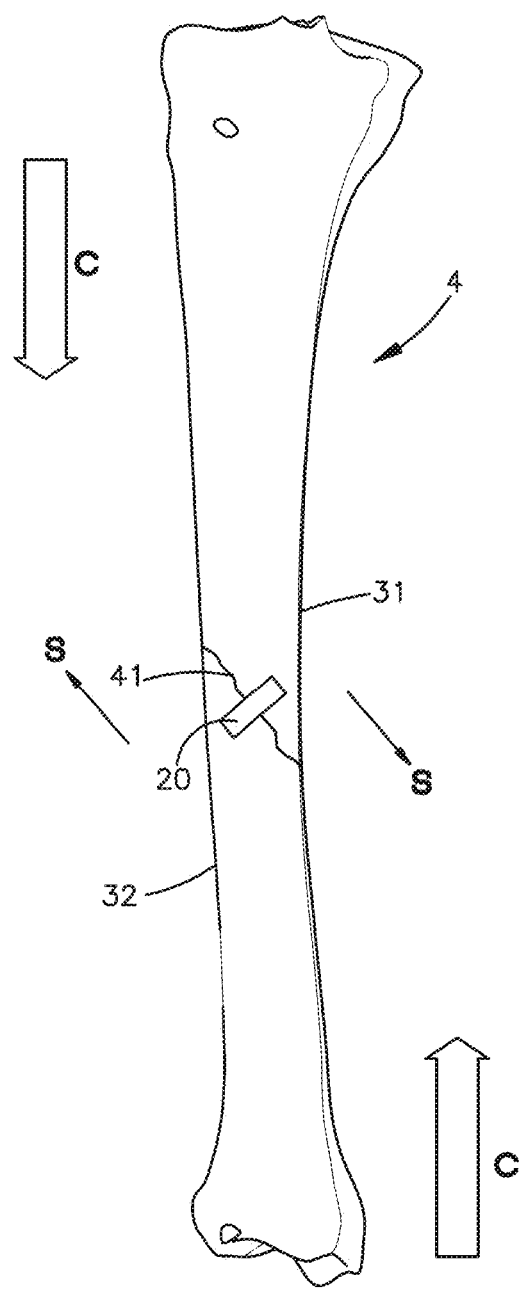
FIG. 10B shows the fracture of FIG. 10A with a continuous compression staple inserted across the fracture boundary in a direction substantially normal to the direction of the shear force according to embodiments of the present disclosure.

With reference to FIGS. 10-11, according to certain embodiments, the application of temporary compressive force C to the first 31 and second 32 bone fragments of long bone 4 can create a shear force S at fracture boundary 41 that is configured to force translation of the first 31 and second 32 bone fragments relative to each other in the direction of the shear force S. In other words, due to the presence of shear force created by the compression, slippage or an over rotation of one bone fragment relative to the other can occur that can result in a misalignment of the long bone and an impairment to the proper healing of the bone. For example, oblique, spiral, segmental (including wedge), and comminuted fractures can all include a fracture boundary (or multiple fracture boundaries) that, upon application of a temporary compression force may cause bone fragments to slip out of alignment. This is primarily due to the orientation of the angle between the bone fragments at the fracture boundary where a steeper angle between the bone fragments increases the transmission of shear forces upon compression FIG. 10A shows the application of temporary compressive force C to an oblique fracture in the diaphyseal region of a tibia 4 that can create a shear force S. In certain embodiments, and with reference to FIG. 10B, the continuous compressive force of the at least one compression staple 20 applies a net compressive force across fracture boundary 41 that is substantially normal to the direction of shear force S, and the net compressive force neutralizes, or otherwise cancels out the shear force S.

Figure 11A:
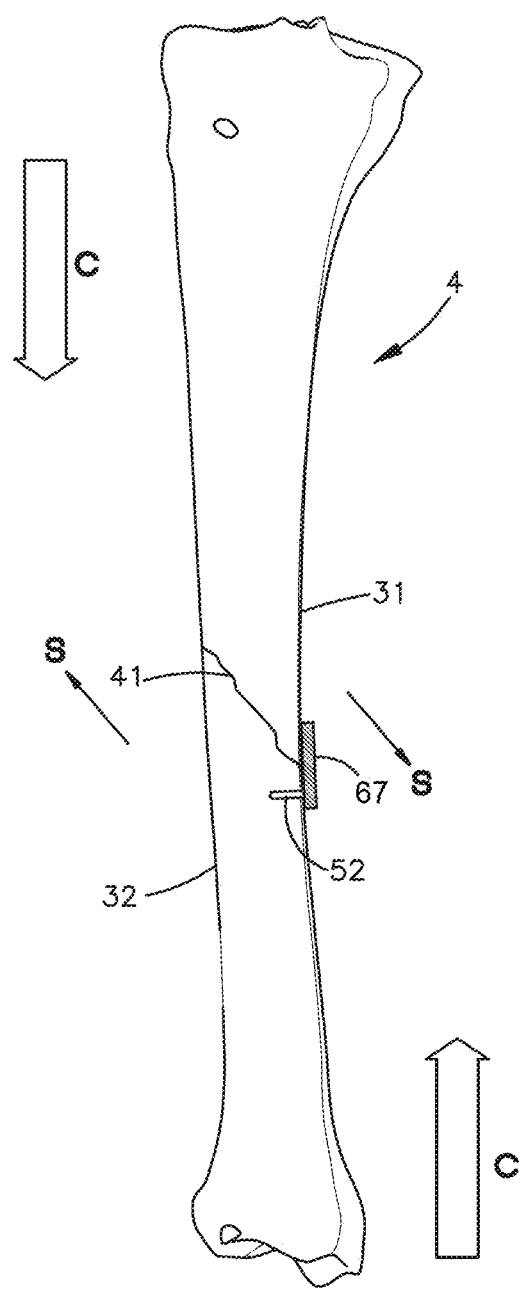
FIG. 11A is a schematic front view of the oblique fracture of FIG. 10A, with a buttress plate applied across the fracture boundary and secured to the second bone fragment according to embodiments of the present disclosure.

With reference to FIG. 11A, according to certain additional embodiments, the methods describe herein can further include:

prior to inserting the at least one compression staple, applying a buttress plate to the first and second bone fragments such that the buttress plate traverses the fracture boundary, and, securing the buttress plate with fastener to only one of the first or second bone fragments such that the other of the first or second bone fragments is not secured to the buttress plate;

where the buttress plate is configured to inhibit the translation of the first and second bone fragments in the direction of the shear force.

Figure 11B:
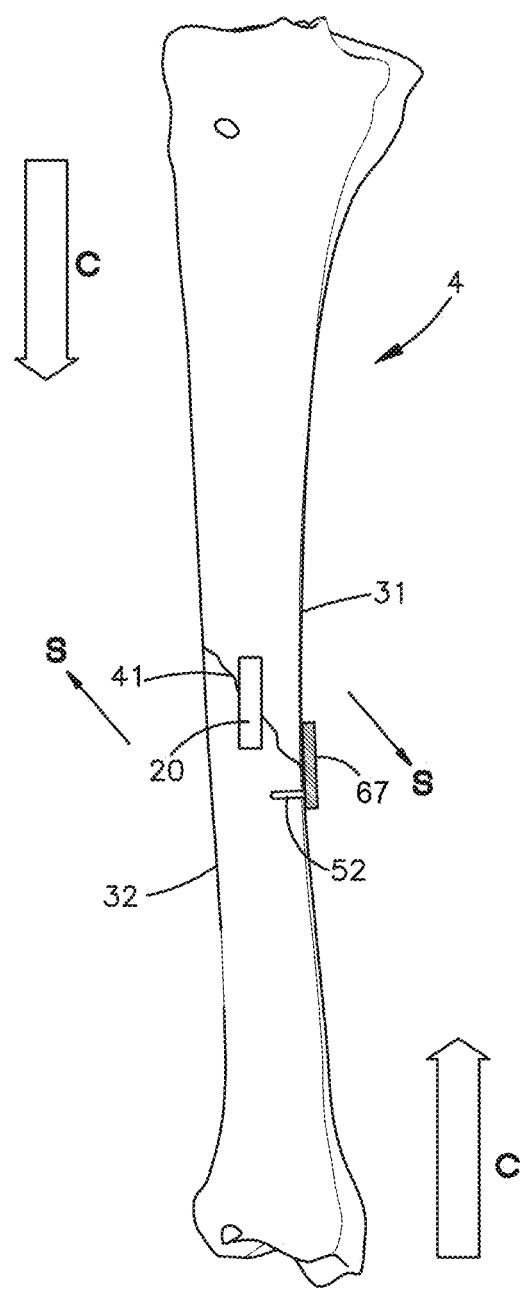
FIG. 11B is schematic front view of FIG. 11A with a continuous compression staple inserted traversing the fracture boundary according to embodiments of the present disclosure.

In these embodiments, and as shown in FIG. 11A, buttress plate 67 functions as a mechanical stop. As shown, tibia 4 has an oblique fracture boundary 41 in the diaphyseal region that is being subjected to temporary compression C that results in shear force S generated at fracture boundary 41. In this case, shear force S is forcing translation of first bone fragment 31 downwards and to the right, and second bone fragment 32 upwards and to the left. Buttress plate 67 is applied to tibia 4 such that it traverses fracture boundary 41 and is secured with a fastener 52 (for example with a bone screw) to second bone fragment 32. Buttress plate 67 therefore resists the ability of first 31 and second 32 bone fragments to translate in the direction of shear and stabilizes the alignment of tibia 4 in anatomically correct configuration. As shown in FIG. 11B, compression staple 20 can then be applied as previously described. In the particular example shown in FIG. 11B, compression staple 20 is inserted in a direction substantially parallel to the compressive force C. The benefit of buttress plate 67 is that it gives more freedom to the surgeon as to placement and orientation of compression staple 20 at fracture boundary 41 because the effects of shear force S no longer need to be taken into account in determining where or how to insert compression staple 20. For example, compression staple 20 could be inserted in a direction substantially normal to fracture boundary 41, if desired.

According to still other embodiments of the present disclosure, a fracture boundary may require more than one compression staple to be inserted to provide appropriate compression to first and second bone fragments. In such embodiments, the at least one compression staple includes a first compression staple and a second compression staple and the step of inserting at least one compression staple and the step of releasing tension in the at the least one compression staple includes:

inserting the first compression staple into the first and second bone fragments such that the first compression staple traverses the fracture boundary, where the first compression staple is inserted in a first tensioned state;

releasing tension in the first compression staple such that the first compression staple transitions from the first tensioned state to a second compressed state that exerts a continuous compressive force to the first and second bone fragments;

inserting the second compression staple into the first and second bone fragments such that the second compression staple traverses the fracture boundary, where the second compression staple is inserted in a first tensioned state; and releasing tension in the second compression staple such that the second compression staple transitions from the first tensioned state to a second compressed state that exerts a continuous compressive force to the first and second bone fragments.

Figure 12A:
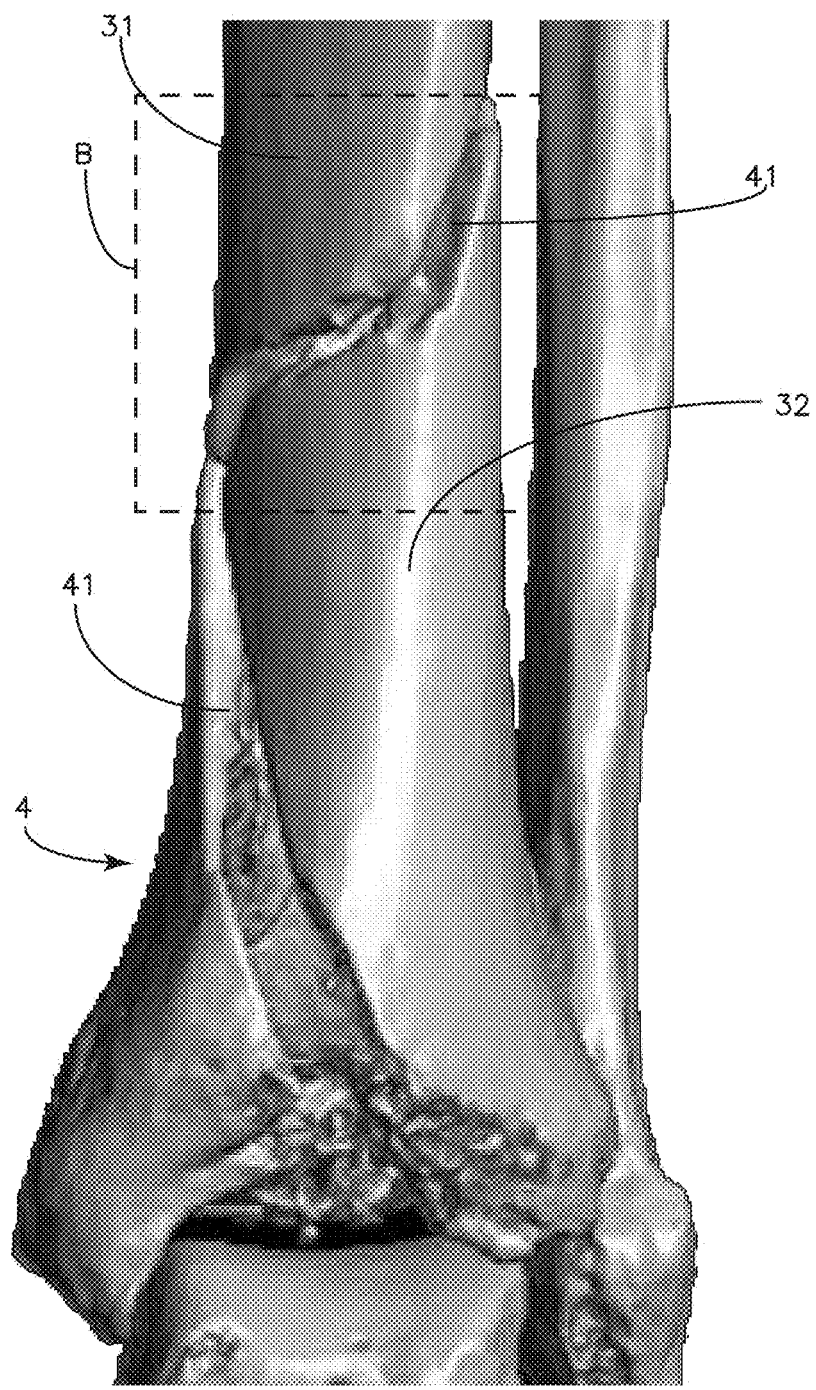
FIG. 12A is front view CT scan image of a right distal tibia with a comminuted Pilon fracture including a spiral fracture boundary.
Figure 12B:
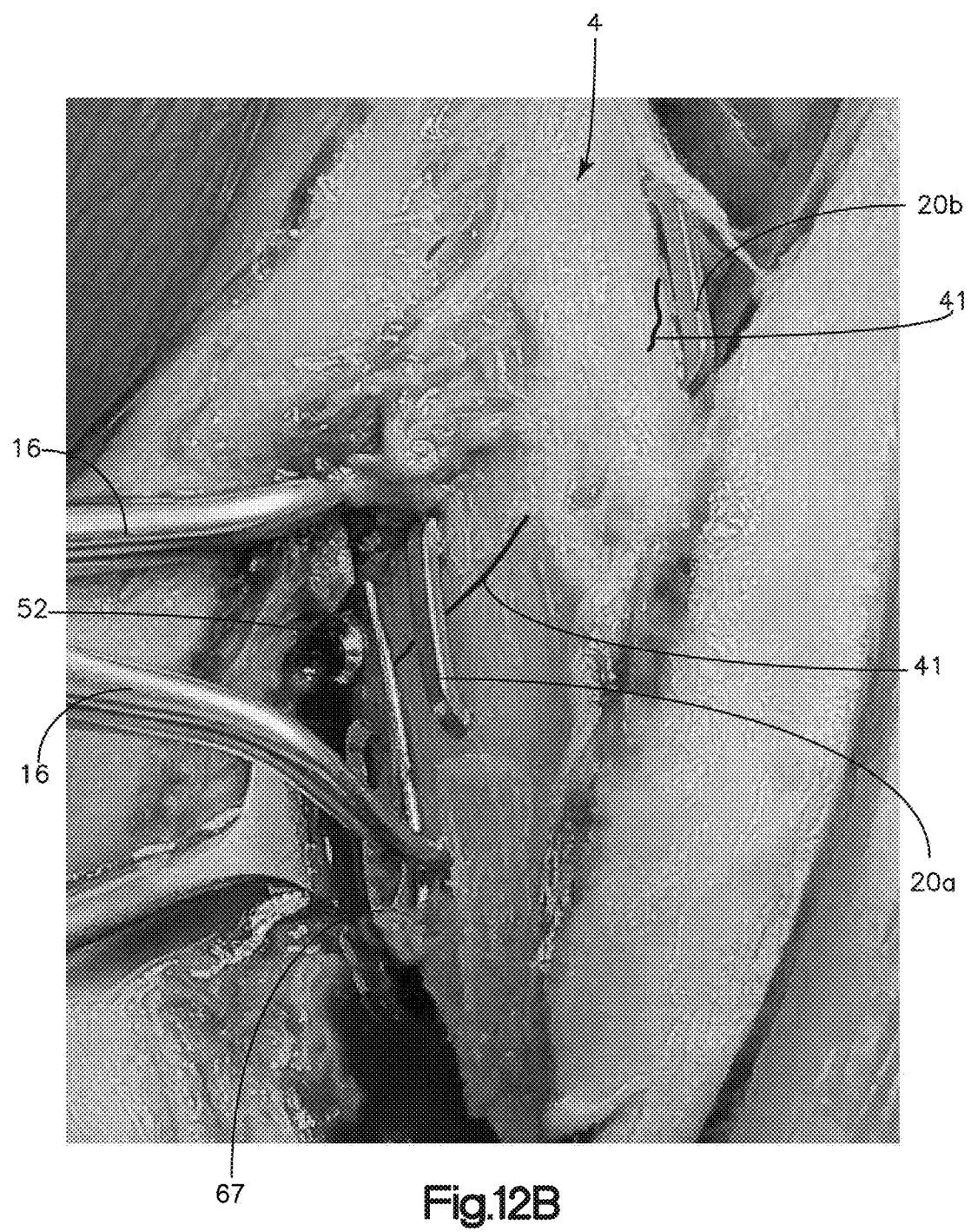
FIG. 12B is an enlarged photographic view of the dashed box "B" shown in FIG. 11A showing the application of temporary compressive force by bone reduction forceps, a buttress plate applied across the fracture boundary and secured to the first bone fragment and a first and a second continuous compression staple inserted across the fracture boundary according to embodiments of the present disclosure.

Referring to FIGS. 12A-B, a comminuted fracture of the right distal tibia of a male is shown, classified according to the AO Classification as a 43C3, which includes multifragmentary fractures of the metaphyseal and articular regions of the distal tibia. This fracture is commonly known as a Pilon fracture. FIG. 12A is a pre-operative CT scan of a distal portion of the fractured tibia 4 showing first 31 and second 32 bone fragments defining a spiral fracture boundary 41. FIG. 12B is an enlarged photograph of the region identified in FIG. 12A with the dashed box B. As shown in FIG. 12B, compression is being applied to tibia 4 with forceps 16 to align first 31 and second 32 bone fragments in anatomical position. First compression staple 20a, and a second compression staple 20b have been inserted into first 31 and second 32 bone fragments traversing fracture boundary 41. First compression staple 20a has been inserted such that it traverses fracture boundary 41 in a direction substantially normal to fracture boundary 41. Second compression staple 20b has been inserted such that it traverses fracture boundary 41 in a direction substantially parallel to the temporary compressive force.

The fracture boundary 41 in the region shown in FIGS. 12A-B is in a spiral fracture configuration and as such the alignment and compression of first 31 and second 32 bone fragments can, in certain embodiments, generate shear force along portions of fracture boundary 41. In this exemplary surgical procedure, and as shown in FIG. 12B, buttress plate 67 has been applied to first 31 and second 32 bone fragments traversing fracture boundary 41 and secured to first bone fragment 31 with a fastener 52 (such as in the manner previously described above with the use of a bone screw). It should be appreciated however, that in alternative embodiments, first 20a and second 20b compression staples can be inserted such that the continuous compressive force of the first 20a and second 20b compression staples exerts a combined net compressive force applied across fracture boundary 41 that is substantially normal to the direction of shear force. In such embodiments, a surgeon can forgo the use of buttress plate 67 if desired because the continuous compression staples 20a, 20b have neutralized the shear force to an extent to eliminate translation of first 31 and second 32 bone fragments.

Figures 13A, 13B, 13C:
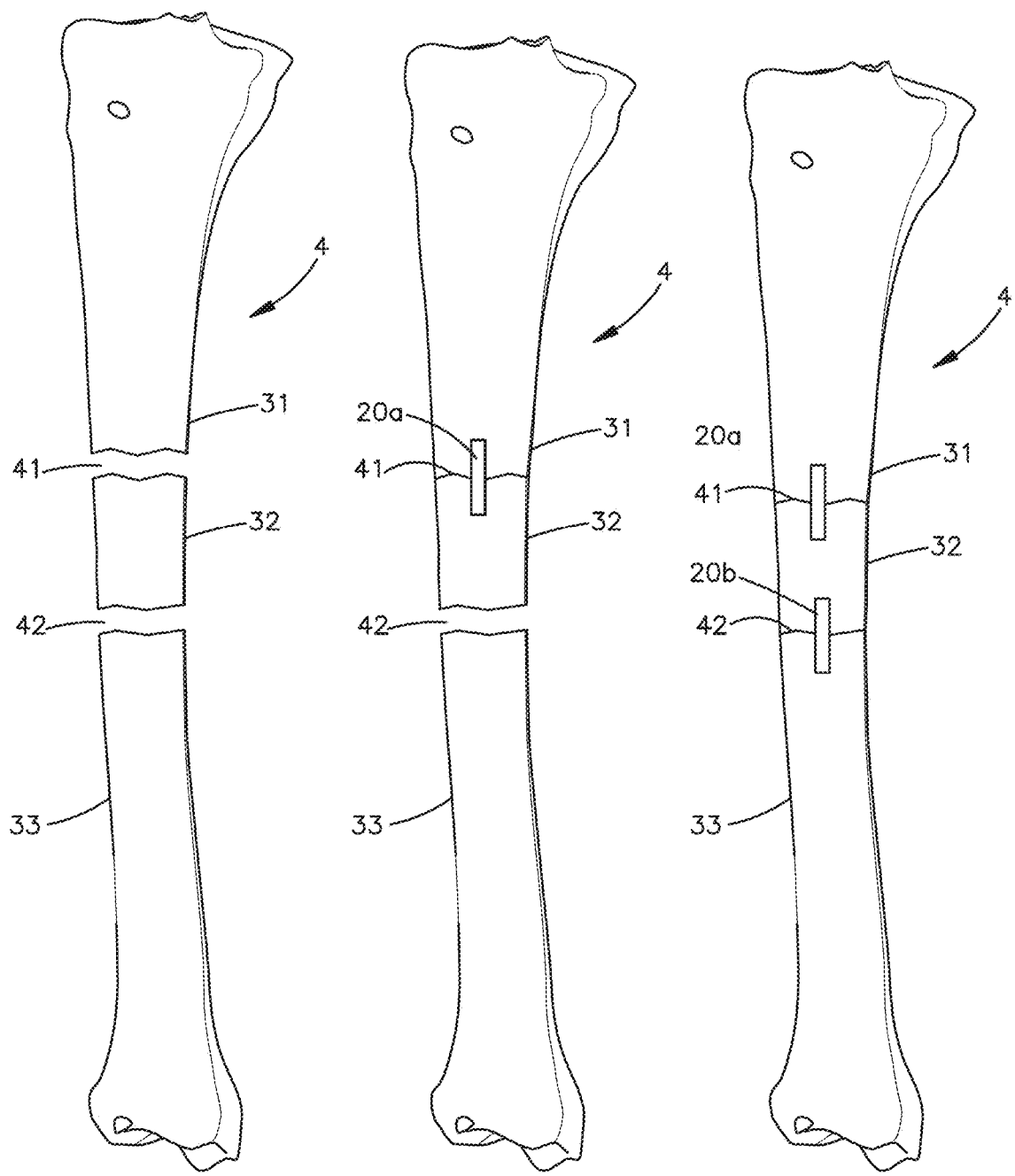
FIGS. 13A-C are schematic front views of a tibia having a multifragmentary fracture with surgical repair shown in sequence according to embodiments described herein; and, FIG. 14 is a top perspective photograph of surgical repair to a long bone showing the application of a neutralization implant according to embodiments of the present disclosure.

As previously described (with respect to FIGS. 3D-E), and with reference to FIGS. 13A-C, certain long bone fractures can include more than two fragments, for example, segmental (including wedge) and comminuted fractures can include at least three bone fragments, such that there can be a first 31, second 32, and third 33 bone fragment. It therefore follows that these multifragmentary fractures will further include more than one fracture boundary, such as a first fracture boundary 41 and a second fracture boundary 42. It should be appreciated that depending upon the severity of the long bone fracture, there can be several bone fragments, for example anywhere from three bone fragments to ten bone fragments at a single long bone fracture site. Likewise, it should be appreciated that as the number of bone fragments at a long bone fracture site increase, the number of fracture boundaries will also increase, most often in proportional relationship to the number of bone fragments, but in certain cases, especially comminuted fractures, there can exist more fracture boundaries than bone fragments because the size and shape of the bone fragments and their respective orientation to one another for alignment and reduction purposes.

According to embodiments of the present disclosure, multifragmentary fractures includes at least a first fracture boundary and a second fracture boundary such that the fracture boundary between the first bone fragment and the second bone fragment is the first fracture boundary and a fracture boundary between a third bone fragment and either of the first bone fragment or the second bone fragment, or both, defines the second fracture boundary. Furthermore, the at least one compression staple includes at least a first compression staple and a second compression staple such the first compression staple is the compression staple inserted at the first fracture boundary. The method of surgical repair, according to these embodiments, can therefore further include the steps of:

aligning the third bone fragment to contact either of the first bone fragment or the second bone fragment, or both, along at least a portion of the second fracture boundary in anatomically correct position;

applying a temporary compressive force to the third bone fragment and either of the first bone fragment or the second bone fragment, or both;

during the application of the temporary compressive force to the third bone fragment, inserting the second compression staple into the third bone fragment such that the second compression staple traverses the second fracture boundary, wherein the second compression staple is inserted in a first tensioned state; and, releasing tension in the second compression staple such that the second compression staple transitions from the first tensioned state to a second compressed state that exerts a continuous compressive force to the third bone fragment and either of the first bone fragment or the second bone fragment, or both.

FIGS. 13A-C show an exemplary illustration of the above surgical steps for a segmental fracture of tibia 4. Here, first 31 and second 32 bone fragments define a first fracture boundary 41, and a second fracture boundary 42 can be defined between second 32 and third 33 bone fragments. It should be appreciated, as previously detailed, that second fracture boundary 42 can be defined between third bone fragment 33, and either of first 31 or second 32 bone fragments, depending upon the orientation of the respective bone fragments at the fracture site.

FIG. 13A is a representation of the unrepaired segmental fracture previously shown in FIG. 3D. FIG. 13B shows the segmental fracture after first 31 and second 32 bone fragments have been aligned at fracture boundary 41 and first compression staple 20a has been inserted to traverse fracture boundary 41 according to the embodiments previously described above. FIG. 13C shows the alignment of third bone fragment 33 with second bone fragment 32 at second fracture boundary 42 and second compression staple 20b has been inserted so as to traverse second fracture boundary 42.

As shown in FIG. 13C, second compression staple 20b has been inserted in a direction substantially normal to second fracture boundary 42. According to another embodiment, second compression staple 20b can be inserted such that it traverses second fracture boundary 42 in a direction substantially parallel to the temporary compressive force. This can be accomplished in the same manner as previously described above.

According to additional embodiments, the application of temporary compressive force to third bone fragment 33 can generate a shear force at second fracture boundary 42, in the same manner as previously described above with respect to the generation of shear force at fracture boundary 41.

According to embodiments of the present disclosure, after completing the steps including the insertion and releasing of tension of the at least one compression staple, the method of surgical repair can include the step of securing a neutralization implant to the long bone, where the neutralization implant defines one or more apertures configured to receive a bone fastener. Such a securing can be done, according to certain embodiments, by applying the bone fastener through the one or more apertures and the long bone such that the fastener secured the neutralization implant to the long bone. In certain embodiments, the neutralization implant can include a bone plate, such as a bridge plate or locking plate, but preferably excludes compression bone plates. In certain other embodiments, the neutralization implant can include an intramedullary nail. It should be appreciated that more than one neutralization implant can be utilized in the surgical constructs and methods described herein, such that multiple bone plates or bone plates in combination with an intramedullary nail can be secured to the long bone.

Figure 14:
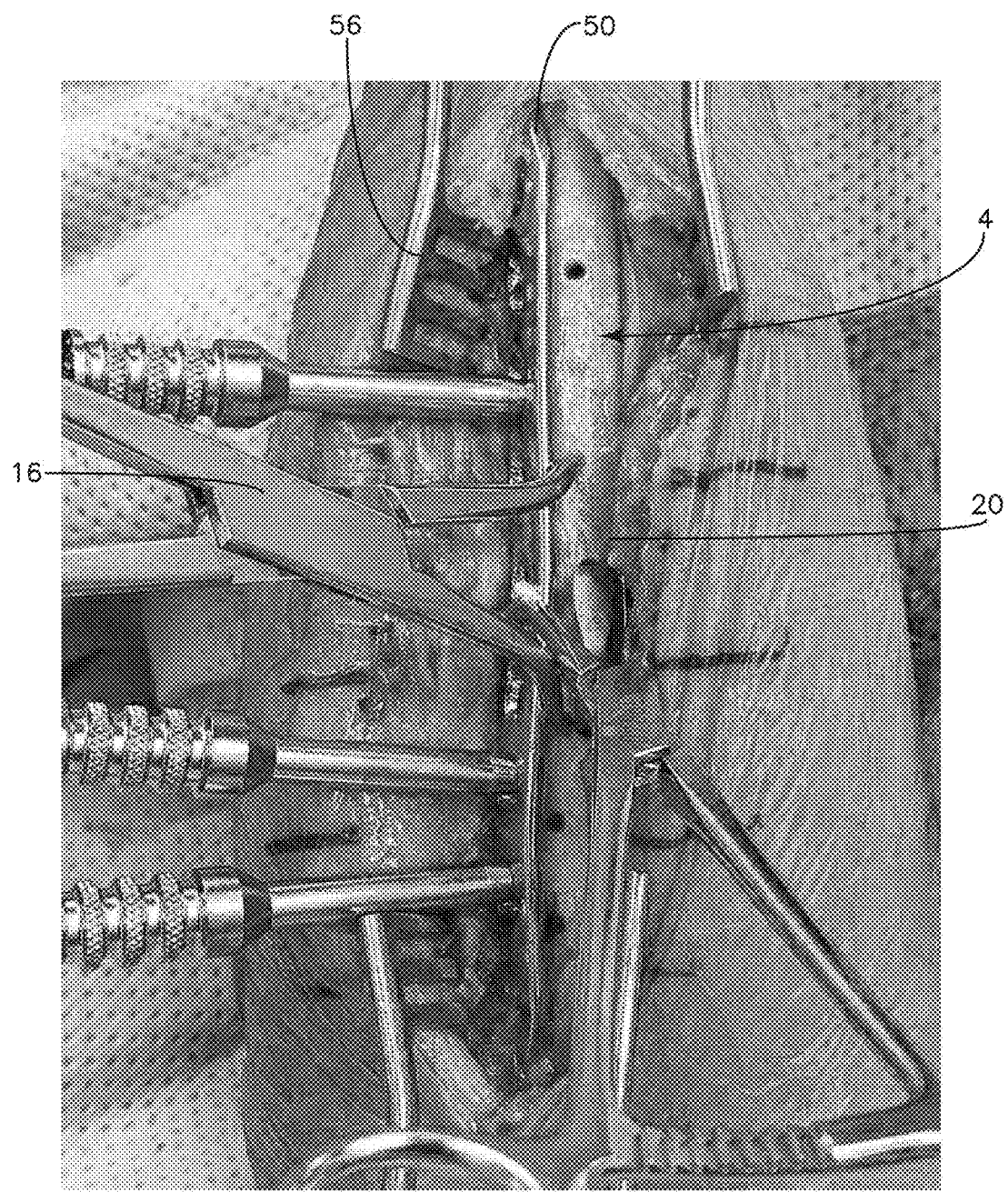

Referring to FIG. 14, neutralization implant 50 (in this case a bone plate) is shown being secured to long bone 4 with fasteners 52 (obstructed by fastener insertion tool) being through apertures 56 into long bone 4. As can be seen, compression staple has already been inserted into long bone 4. Temporary compression is being applied to long bone 4 with bone reduction forceps 16. Depending on the type of long bone fracture and the type of neutralization implant being applied to the long bone, the removal of the temporary compressive force can occur prior to, or subsequent to, the securing of the neutralization implant.

According to further embodiments of the present disclosure, a kit for use in the surgical repair of a long bone fracture is described including:

at least one compression staple configured to traverse a fracture boundary in a long bone between a first bone fragment and a second bone fragment; and, at least one neutralization implant.

In certain embodiments, the kit can additionally include at least one buttress plate. In additional embodiments, the at least one compression staple defines a bridge length extending between the first end and a second, wherein the bridge length is in the range of about 15 mm to about 35 mm. In further embodiments, the first and second leg lengths are each in the range of about 15 mm to about 25 mm. In still further embodiments, the at least one compression staple includes a third leg and a fourth leg, wherein the third leg and fourth leg each extend from the bridge between the first and second legs and in a direction substantially the same as the first leg and second leg.

In certain embodiments, the neutralization implant is a bone plate. In additional embodiments, the neutralization implant is an intramedullary nail.

In certain embodiments, the at least one compression staple of the kit can include one compression staple, two compression staples, three compression staples, up to and including ten compression staples.

According to still further embodiments of the present disclosure, a surgical construct system for use in the surgical repair of a long bone fracture described including:

at least one compression staple configured to traverse a fracture boundary in a long bone between a first bone fragment and a second bone fragment;

at least one buttress plate configured to traverse the fracture boundary and, a neutralization implant.

In additional embodiments, the at least one compression staple defines a bridge length extending between the first end and a second, wherein the bridge length is in the range of about 15 mm to about 35 mm. In further embodiments, the first and second leg lengths are each in the range of about 15 mm to about 25 mm. In still further embodiments, the at least one compression staple includes a third leg and a fourth leg, wherein the third leg and fourth leg each extend from the bridge between the first and second legs and in a direction substantially the same as the first leg and second leg.

In certain embodiments, the neutralization implant is a bone plate. In additional embodiments, the neutralization implant is an intramedullary nail.

The invention claimed is:

1. A method of surgical repair of a long bone utilizing a continuous compression staple comprising:

identifying an orthopedic injury site having a fracture of a long bone suitable for repair utilizing a surgical construct including at least one continuous compression staple, the fracture defining a fracture boundary between a first bone fragment and a second bone fragment of the long bone;

aligning the first bone fragment and the second bone fragment to contact one another along at least a portion of the fracture boundary in anatomically correct position;

applying a temporary compressive force to the first and second bone fragments;

during the application of the temporary compressive force, inserting at least one compression staple into the first and second bone fragments such that the at least one compression staple traverses the fracture boundary, wherein the at least one compression staple is inserted in a first tensioned state;

releasing tension in the at least one compression staple such that the staple transitions from the first tensioned state to a second compressed state that exerts a continuous compressive force to the first and second bone fragments;

securing a neutralization implant to the long bone, the neutralization implant defining one or more apertures configured to receive a bone fastener, by applying the bone fastener through the one or more apertures and the long bone; and, removing the temporary compressive force.

2. The method of claim 1, wherein the step of inserting the at least one compression staple comprises inserting the at least one compression staple such the compression staple traverses the fracture boundary in a direction substantially normal to the fracture boundary.

3. The method of claim 1, wherein the step of inserting the at least one compression staple comprises inserting the at least one compression staple such that the at least one compression staple traverses the fracture boundary in a direction substantially parallel to the temporary compressive force.

4. The method of claim 1, wherein the step of applying the temporary compressive force creates a shear force at the fracture boundary configured to force translation of the first and second bone fragments relative to each other in a direction of the shear force, wherein the continuous compressive force of the at least one compression staple applies a net compressive force across the fracture boundary that is substantially normal to the direction of shear force, and wherein the net compressive force is greater than the shear force.

5. The method of claim 1, wherein the step of applying the temporary compressive force creates a shear force at the fracture boundary configured to force translation of the first and second bone fragments relative to each other in a direction of the shear force, the method further comprising:
prior to inserting the at least one compression staple, applying a buttress plate to the first and second bone fragments such that the buttress plate traverses the fracture boundary, and
securing the buttress plate to only one of the first or second bone fragments such that the other of the first or second bone fragments is not secured to the buttress plate;
wherein the buttress plate is configured to inhibit the translation of the first and second bone fragments in the direction of the shear force.

6. The method of surgical repair of claim 1, wherein the at least one compression staple comprises a first compression staple and a second compression staple and wherein the step of inserting at least one compression staple and the step of releasing tension in the at the least one compression staple comprises:
inserting the first compression staple into the first and second bone fragments such that the first compression staple traverses the fracture boundary, wherein the first compression staple is inserted in a first tensioned state;
releasing tension in the first compression staple such that the first compression staple transitions from the first tensioned state to a second compressed state that exerts a continuous compressive force to the first and second bone fragments;
inserting the second compression staple into the first and second bone fragments such that the second compression staple traverses the fracture boundary, wherein the second compression staple is inserted in a first tensioned state; and
releasing tension in the second compression staple such that the second compression staple transitions from the first tensioned state to a second compressed state that exerts a continuous compressive force to the first and second bone fragments.

7. The method of claim 6, wherein the step of inserting the second compression staple comprises inserting the second compression staple such that the second compression staple traverses the fracture boundary in a direction substantially normal to the fracture boundary.

8. The method of claim 6, wherein the step of inserting the second compression staple comprises inserting the second compression staple such the second compression staple traverses the fracture boundary in a direction substantially parallel to the temporary compressive force.

9. The method of claim 6, wherein the step of applying the temporary compressive force creates a shear force at the fracture boundary configured to force translation of the first and second bone fragments relative to each other in a direction of the shear force, and wherein the continuous compressive force of the first and second compression staples exerts a combined net compressive force applied across the fracture boundary that is substantially normal to the direction of shear force.

10. The method of claim 1, wherein the fracture includes at least a first fracture boundary and a second fracture boundary such that the fracture boundary between the first bone fragment and the second bone fragment is the first fracture boundary and a fracture boundary between a third bone fragment and either of the first bone fragment or the second bone fragment, or both, defines the second fracture boundary; and wherein the at least one compression staple comprises at least a first compression staple and a second compression staple such the first compression staple is the compression staple inserted at the first fracture boundary; the method further comprising:
aligning the third bone fragment to contact either of the first bone fragment or the second bone fragment, or both, along at least a portion of the second fracture boundary in anatomically correct position;
applying a temporary compressive force to the third bone fragment and either of the first bone fragment or the second bone fragment, or both;
during the application of the temporary compressive force to the third bone fragment, inserting the second compression staple into the third bone fragment such that the second compression staple traverses the second fracture boundary, wherein the second compression staple is inserted in a first tensioned state; and,
releasing tension in the second compression staple such that the second compression staple transitions from the first tensioned state to a second compressed state that exerts a continuous compressive force to the third bone fragment and either of the first bone fragment or the second bone fragment, or both.

11. The method of claim 10, wherein the step of inserting the second compression staple comprises inserting the second compression staple such the second compression staple traverses the second fracture boundary in a direction substantially normal to the second fracture boundary.

12. The method of claim 10, wherein the step of inserting the second compression staple comprises inserting the second compression staple such the second compression staple traverses the second fracture boundary in a direction substantially parallel to the temporary compressive force to the third bone fragment.

13. The method of claim 10, wherein the temporary compressive force applied to the third bone fragment generates a shear force at the second fracture boundary, and wherein the step of inserting the second compression staple comprises inserting the second compression staple such the second compression staple traverses the second fracture boundary in a direction substantially normal to a direction of shear force.

14. The method of claim 10, wherein the applying of the temporary compressive force creates a shear force at the second fracture boundary between the third bone fragment and, the first bone fragment or the second bone fragment or both, the method further comprising:
   prior to inserting the second compression staple, applying a buttress plate to the third bone fragment and either of the first bone fragment or the second bone fragment such that the buttress plate traverses the second fracture boundary, and
   securing the buttress plate to only one of the third bone fragment or the first or second bone fragments such that the other of the third bone fragment or the first or second bone fragments is not secured to the buttress plate;
   wherein the buttress plate is configured to inhibit movement of the third bone fragment in a direction of the shear force.

15. The method of claim 10, wherein the fracture is a comminuted fracture, and:
   (i) the first fracture boundary defines a transverse fracture angle between the first bone fragment and the second bone fragment;
   (ii) the first fracture boundary defines an oblique fracture angle between the first bone fragment and the second bone fragment;
   (iii) the second fracture boundary defines a transverse fracture angle between the third bone fragment and either of the first or second bone fragments; or
   (iv) the second fracture boundary defines an oblique fracture angle between the third bone fragment and either of the first or second bone fragments.

16. The method of claim 10, wherein the fracture is a segmental fracture, and:
   (i) the first fracture boundary defines a transverse fracture angle between the first bone fragment and the second bone fragment;
   (ii) the first fracture boundary defines an oblique fracture angle between the first bone fragment and the second bone fragment;
   (iii) the second fracture boundary defines a transverse fracture angle between the third bone fragment and either of the first or second bone fragments; or
   (iv) the second fracture boundary defines an oblique fracture angle between the third bone fragment and either of the first or second bone fragments.

17. The method of claim 1, wherein the neutralization implant is a bone plate or an intramedullary nail.

18. The method of claim 17, wherein the neutralization implant is a bone plate.

19. The method of claim 17, wherein the neutralization implant is an intramedullary nail.

20. The method of claim 17, wherein the neutralization implant further comprises one or more bone screws.

21. The method of claim 1, wherein at least a portion of the fracture boundary is located at a diaphyseal region of the long bone.

22. The method of claim 1, wherein at least a portion of the fracture boundary is located at an articular region of the long bone.

23. A method of surgical repair of a long bone utilizing a surgical construct including at least one continuous compression staple and a buttress plate, the method comprising:
   identifying an orthopedic injury site having a fracture of a long bone, the fracture defining a fracture boundary between a first bone fragment and a second bone fragment of the long bone;
   aligning the first bone fragment and the second bone fragment to contact one another along at least a portion of the fracture boundary in anatomically correct position;
   applying a temporary compressive force to the first and second bone fragments such that a shear force is created at the fracture boundary configured to force translation of the first and second bone fragments relative to each other in a direction of the shear force;
   during the application of the temporary compressive force, applying a buttress plate to the first and second bone fragments such that the buttress plate traverses the fracture boundary, and securing the buttress plate to only one of the first or second bone fragments such that the other of the first or second bone fragments is not secured to the buttress plate, wherein the buttress plate is configured to inhibit the translation of the first and second bone fragments in the direction of the shear force;
   during the application of the temporary compressive force, inserting at least one compression staple into the first and second bone fragments such that the at least one compression staple traverses the fracture boundary, wherein the at least one compression staple is inserted in a first tensioned state;
   releasing tension in the at least one compression staple such that the staple transitions from the first tensioned state to a second compressed state that exerts a continuous compressive force to the first and second bone fragments; and,
   removing the temporary compressive force.

24. The method of claim 23, wherein the fracture boundary defines an oblique fracture angle between the first bone fragment and the second bone fragment.

25. The method of claim 23, wherein the fracture is a spiral fracture.

* * * * *